US008383681B2

(12) United States Patent
Roberts et al.

(10) Patent No.: US 8,383,681 B2
(45) Date of Patent: Feb. 26, 2013

(54) DROXIDOPA AND PHARMACEUTICAL COMPOSITION THEREOF FOR THE TREATMENT OF MOOD DISORDERS, SLEEP DISORDERS OR ATTENTION DEFICIT DISORDERS

(75) Inventors: Michael J. Roberts, Charlotte, NC (US); Simon Pedder, Fort Mill, SC (US)

(73) Assignee: Chelsea Therapeutics, Inc., Charlotte, NC (US)

( * ) Notice: Subject to any disclaimer, the term of this patent is extended or adjusted under 35 U.S.C. 154(b) by 579 days.

(21) Appl. No.: 12/116,560

(22) Filed: May 7, 2008

(65) Prior Publication Data
US 2009/0023705 A1 Jan. 22, 2009

(51) Int. Cl.
A61K 31/195 (2006.01)
A61K 31/19 (2006.01)
A61K 31/135 (2006.01)

(52) U.S. Cl. ........................................ 514/567; 514/653

(58) Field of Classification Search .................. 514/567, 514/653
See application file for complete search history.

(56) References Cited

U.S. PATENT DOCUMENTS

| | | | |
|---|---|---|---|
| 3,920,728 A | 11/1975 | Hegedüs et al. | |
| 4,246,428 A | 1/1981 | Ohashi et al. | |
| 4,319,046 A | 3/1982 | Vacek | |
| 4,330,558 A | 5/1982 | Suzuki et al. | |
| 4,421,767 A | 12/1983 | Palfreyman et al. | |
| 4,480,109 A | 10/1984 | Ohashi et al. | |
| 4,497,826 A | 2/1985 | Narabayashi et al. | |
| 4,529,603 A | 7/1985 | Mori et al. | |
| 4,562,263 A | 12/1985 | Ohashi et al. | |
| 4,647,587 A | 3/1987 | Katsube et al. | |
| 4,690,949 A | 9/1987 | Yoshida et al. | |
| 4,699,879 A | 10/1987 | Umezawa et al. | |
| 4,963,590 A | 10/1990 | Bäckström et al. | |
| 5,015,564 A | 5/1991 | Chari | |
| 5,015,654 A | 5/1991 | Al-Damluji | |
| 5,240,930 A | 8/1993 | Al-Damluji | |
| 5,266,596 A | 11/1993 | Yokokawa et al. | |
| 5,616,618 A | 4/1997 | Takagi | |
| 5,656,669 A | 8/1997 | Nishino | |
| 5,739,387 A | 4/1998 | Oda et al. | |
| 5,864,041 A | 1/1999 | Oda et al. | |
| 6,033,993 A | 3/2000 | Love, Jr. et al. | |
| 6,150,412 A | 11/2000 | Pystynen et al. | |
| 6,387,936 B1 | 5/2002 | Blanchard-Bregeon et al. | |
| 6,512,136 B1 | 1/2003 | Benes et al. | |
| 6,610,324 B2 | 8/2003 | Stoll | |
| 6,610,690 B2 | 8/2003 | Wong et al. | |
| 6,653,325 B2 | 11/2003 | Svensson | |
| 6,703,424 B2 | 3/2004 | Levin et al. | |
| 6,746,688 B1 | 6/2004 | Kushnir et al. | |
| 6,929,801 B2 | 8/2005 | Klose et al. | |
| 6,992,110 B2 | 1/2006 | Kranzler et al. | |
| 2001/0007856 A1 | 7/2001 | Nishino | |
| 2001/0047032 A1 | 11/2001 | Castillo et al. | |
| 2002/0177593 A1 | 11/2002 | Ishihara et al. | |
| 2003/0181509 A1 | 9/2003 | Hinz | |
| 2004/0013620 A1 | 1/2004 | Klose et al. | |
| 2004/0152760 A1 | 8/2004 | Castillo et al. | |
| 2005/0043408 A1 | 2/2005 | Yeboah et al. | |
| 2005/0096387 A1 | 5/2005 | Verheijen et al. | |
| 2005/0233010 A1 | 10/2005 | Satow | |
| 2006/0035976 A1* | 2/2006 | Peroutka ........................ 514/567 |
| 2007/0004639 A1 | 1/2007 | Kane et al. | |
| 2009/0074861 A1 | 3/2009 | Ochiai et al. | |

FOREIGN PATENT DOCUMENTS

| | | |
|---|---|---|
| EP | 0237 929 | 9/1987 |
| GB | 2 200 109 A | 7/1988 |
| WO | WO 2004/032844 A2 | 4/2004 |
| WO | WO 2004/100929 A1 | 11/2004 |
| WO | WO 2005/085178 A | 9/2005 |
| WO | WO 2007/112014 A2 | 10/2007 |
| WO | WO 2008/003028 A2 | 1/2008 |

OTHER PUBLICATIONS

Morissette et al., Adv. Drug Del. Rev. 56 (2004), 275-300.*
Vippagunta et al., Adv. Drug. Del. Rev. 48 (2001), 3-26.*
NIH—National Institute of Neurological Disorders and Stroke: information sheet on orthostatic hypotension (2007). Accessed online Aug. 30, 2010 at http://www.ninds.nih.gov/disorders/orthostatic_hypotension/orthostatic_hypotension.htm?css=print.*
Webster's Online Dictionary. Definition of ischemia. Accessed online Aug. 30, 2010 at http://www.websters-dictionaryonline.org/definitions/ischemia?cx=partner-pub-0939450753529744%3Av0qd01-tdlq&cof=FORID%3A9&ie=UTF-8&q=ischemia&sa=Search.*
Kaufmann et al. Norepinephrine precursor therapy in neurogenic orthostatic hypotension. Circulation 108, 724-28 (2003).*
Brannan et al. L-threo-DOPS increases extracellular norepinephrine levels in the brain: an in vivo study. Neurology 40(7), 1134-5 (1990) (abstract).*

(Continued)

Primary Examiner — Barbara P Badio
Assistant Examiner — Sara E Townsley
(74) Attorney, Agent, or Firm — Womble Carlyle Sandridge & Rice, LLP

(57) ABSTRACT

The present invention provides pharmaceutical compositions comprising droxidopa alone, or in combination with one or more further active ingredients, for the treatment of conditions, such as mood disorders, sleep disorders, or attention deficit disorders. In certain embodiments, the compositions useful in the methods of the invention comprise droxidopa and a compound selected from the group consisting of DOPA decarboxylase inhibiting compounds, catechol-O-methyl-transferase inhibiting compounds, cholinesterase inhibiting compounds, monoamine oxidase inhibiting compounds, norepinephrine reuptake inhibiting compounds, selective serotonin reuptake inhibiting compounds, tricyclic antidepressant compounds, serotonin norepinephrine reuptake inhibiting compounds, norepinephrine dopamine reuptake inhibiting compound, noradrenergic and specific serotonergic antidepressants, and combinations thereof. The inventive compositions are particularly useful in the treatment of depression, narcolepsy, insomnia, and Attention Deficit/Hyperactivity Disorder (AD/HD).

10 Claims, 2 Drawing Sheets

OTHER PUBLICATIONS

Goldstein, "L-Dihydroxphenylserine (L-DOPS): A Norepinephrine Prodrug," *Cardiovascular Drug Reviews*, 2006, pp. 189-203, vol. 24, No. 3-4.

Mathias et al., "L-Threo-dihydroxyphenylserine(L-threo-DOPS; droxidopa) in the management of Neurogenic Orthostatic Hypotension: A Multi-National, Multi-Center, Dose-Ranging Study in Multiple System Atrophy and Pure Autonomic Failure," *Clinical Autonomic Research: Official Journal of the Clinical Autonomic Research Society*, 2001, pp. 235-242, vol. 11, No. 4.

Goswami et al., "Characterization of a Flavoprotein Iodotyrosine Deiodinase from Bovine Thyroid," *The Journal of Biological Chemistry*, 1979, pp. 12326-12330, vol. 254, No. 24.

Komiya et al., "The Effectivity of L-threo-3,4-dihydroxyphenylserine (L-threo-DOPS) to the Hypersomnia and the Subcortal Dementia Caused by Bilateral Medial Thalamic and Midbrain Infarcts" *Clin. Neurol.*, 1988, pp. 268-271, vol. 28, No. 3.

Agmo et al., "A Rat Model of Distractibility: Effects of Drugs Modifying Dopaminergic, Noradrenergic and GABA Ergic Neurotransmission," *Journal of Neural Transmission*, 1997, pp. 11-29, Vo. 104, No. 1. http://www.springerlink.com/content/n66254211q511485/.

Bennett, et al., "A Peripheral Mononeuropathy in Rat That Produces Disorders of Pain Sensation Like Those Seen in Man," *Pain*, 1988, pp. 87-107, vol. 33, No. 1.

Bradley et al., "Orthostatic Hypotension," *American Family Physician*, 2003, pp. 2393-2398, vol. 68, No. 12.

Brzostowska et al., "Phenylcarbamates of (+)-Eseroline, (+)-N1-Noreseroline and (+)-Physovenol: Selective Inhibitors of Acetyl and, or Butyrylcholinesterase", *Medical Chemistry Research*, 1992, pp. 238-246, vol. 2, No. 4.

Calkins et al., "Relationship Between Chronic Fatigue Syndrome and Neurally Mediated Hypotension," *Cardiology in Review*. (1998), pp. 125-134, vol. 6, No. 3.

Cryan et al., "Norepinephrine-Deficient Mice Lack Responses to Antidepressant Drugs, Including Selective Serotonin Reuptake Inhibitors," *PNAS*, 2004, pp. 8186-8191, vol. 101, No. 21. www.pnas.org/cgi/doi/10.1073/pnas.0401080101.

Dableh et al., "Antidepressant-like Effects of Neurokinin Receptor Antagonists in the Forced Swim Test in the Rat," *European Journal of Pharmacology*, 2005, pp. 99-105, vol. 507.

Dhir et al., "Effect of Addition of Yohimbine (Alpha-2-Receptor Antagonist) to the Antidepressant Activity of Fluoxetine or Venlafaxine in the Mouse Forced Swim Test," *Pharmacology*, 2007, 239-243, vol. 80.

Edvinsson et al., "Effect of Exogenous Noradrenaline on Local Cerebral Blood Flow After Osmotic Opening of the Blood-Brain Barrier in the Rat," *J. Physiol.*, 1978, pp. 149-156, vol. 274.

Flippen-Anderson et al., Thiaphysovenol Phenylcarbamates: X-ray Structures of Biologically Active and Inactive Anticholinesterase Agents, *Heterocycles*, 1993, pp. 79-86, vol. 36, No. 1.

Goto et al., "Depression in Multiple System Atrophy: A case Report," *Psychiatry and Clinical Neurosciences*, 2000, pp. 507-511, vol. 54.

Greig et al. "Phenserine and Ring C Hetero-Analogues: Drug Candidates for the Treatment of Alzheimer's Disease." *Medicinal Research Reviews*. (1995) vol. 15, No. 1, 3-31.

He et al. "Thiaphysovenine and Carbamate Analogues: A New Class of Potent Inhibitors of Cholinesterases." *Medical Chemistry Research*. (1992) vol. 2, 229-237.

Iida et al., "Effects of L-Threo-3,4-Dihydroxyphenylserine on Orthostatic Hypotension in Hemodialysis Patients," *American Journal of Nephrology*, 2002, pp. 338-346, vol. 22, No. 4, Basel.

Joo, et al., "Cerebral Perfusion Abnormality in Narcolepsy with Cateaplexy," *NeuroImage*, 2005, pp. 410-416, vol. 28, No. 2.

Kato et al., "Reversal of the Reserpine-Induced Ptosis by L-Threo-3,4-Dihydroxy-Phenylserine (L-Threo-DOPS), A (+)-Norepinephrine Precursor, and Its Potentiation by Imipramine or Nialamide," *Naunyn-Schmiedeberg's Archies of Pharmacology*, 1986, pp. 243-246, vol. 332, No. 3, Berlin.

Kato et al., "Studies on the Activity of L-Threo-3,4-Dihydroxyphenylserine (L-DOPS) As a Catecholamine Precursor in the Brain, Comparison With Taat of L-DOPA," *Biochemical Pharmacology*, 1987, pp. 3051-3057, vol. 36, No. 18, Great Britain.

Kawabata et al., "The Noradrenaline Precursor L-Threo-3,4-Dihydroxyphenylserine Exhibits Antinociceptive Activity Via Central Alpha-Adrenoceptors in the Mouse," *Br J Pharmacol*. 1994, pp. 503-508, vol. 111, No. 2, Japan.

Kim et al., "Methylphenidate Increased Regional Cerebral Blood Flow in Subjects with Attention Deficit/Hyperactivity Disorder," *Yonsei Medical Journal*, 2001, pp. 19-29, vol. 42, No. 1.

Lamberti et al., "Antidepressant-like Effects of Endogenous Histamine and of Two Histamine $H_1$ Receptor Agonists in the Mouse Forced Swim Test," *British Journal of Pharmacology*, 1998, pp. 1331-1336, vol. 123.

Lahiri et al. "Cholinesterase Inhibitors, β-Amyloid Precursor Protein and Amyloid β-Peptides in Alzheimer's Disease," *Acta Neurologica Scandinavia*. (Dec. 2000) vol. 102 (s176), 60-67.

Lee et al., "Regional Cerebral Blood Flow in Children With Attention Deficit Hyperactivity Disorder: Comparison Before and After Methylphenidate Treatment," *Human Brain Mapping*, 2005, pp. 157-164, vol. 24, No. 3.

Lou et al., "Focal Cerebral Hypoperfusion in Children With Dysphasia and/or Attention Deficit Disorder," *Archives of Neurology*, 1984, pp. 825-829, vol. 41, No. 8.

Moldes et al. "The Actions of Dihydroxyphenylalanine and Dihydroxyphenylserine on the Sleep-Wakefulness Cycle of the Rat After Peripheral Decarboxylase Inhibition," *Br J Pharmacol*, 1975, pp. 101-106, vol. 54, No. 1.

Mori et al., "Effects of L-Erythro-3, 4-Dihydroxyphenylserine on Sleep-Wakefulness Patterns and Concentrations of Brain Catecholamines and Serotonin in Rats," *Jpn J Psychiatry Neurol*, 1987, pp. 301-310, vol. 41, No. 2.

Noto et al., "Effects of L-Threo- and Erythro-3,4-Dihydroxyphenylserine on Learning Performance and Concentrations of Brain Noradrenaline and Its Metabolites in Rats," *Pharmacol Biochem Behav.*, 1992, pp. 215-221, Vo. 43, No. 1.

Pei et al. "Total Synthesis of Racemic and Optically Active Compounds Related to Physostigmine and Ring-C Heteroanalogues from 3'[-(Dimethylamino0ethyl]-2,3-dihydro-5-methoxy-1, 3-dimentyl-1H-indol-2-oL" *Helvetica Chimica ACTA*. (1994) vol. 77.

Rowe et al., "Is Neurally Mediated Hypotension an Unrecognised Cause of Chronic Fatigue?" *The Lancet*, 1995, pp. 623-624, vol. 345.

Russell, "Advances in Fibromyalgia: Possible Role for Central Neurochemicals," *Am J Med Sci.*, 1998, pp. 377-384, vol. 315, No. 6.

Porsolt et al., "Behavioural Despair in Mice: A primary Screening Test for antidepressants," *Arch. Int. Pharmacodyn*, 1977, pp. 327-336, vol. 229.

Schondorf, "Acetylcholinesterase Inhibition in the Treatment of Hypotension," *Journal of Neurology Neurosurgery and Psychiatry*, 2003, pp. 1187, vol. 74, No. 9, www.jnnp.bmjjournals.com.

Singer et al. "Pyridostigmine Treatment Trial in Neurogenic Orthostatic Hypotension", 2006, *Archives of Neurology*, vol. 63, No. 4, pp. 513-518, www.archneur.ama-assn.org.

Takagi et al., "Analgesic Effect of L-Threo-3,4-Dihydroxyphenylserine (L-DOPS) in Patients With Chronic Pain," *Eur Neuropsychophamacol.*, 1996, pp. 43-47, vol. 6, No. 1, Japan.

Tanaka et al., "The Effects of the Noradrenaline Precursor, L-Threo-3,4-Dihydroxy-Phenylserine, in Children With Orthostatic Intolerance," *Clinical Autonomic Research*, 1996, pp. 189-193, vol. 6.

Toda et al., "Parkinson Disease Patient with Fibromyalgia: A Case Report" *Parkinsonism and Related Disorders*, 2007, pp. 312-312, vol. 13.

Tulen et al., "Sleeping With and Without Norepinephrine: Effects of Metoclopramide and D,L-Threo-3,4- Dihydroxyphenylserine on Sleep in Dopamine Beta-Hydroxylase Deficiency," *Sleep*, 1991, pp. 32-38, vol. 14, No. 1. The Netherlands.

Verhagen-Kamerbeek, et al. "Attenuation of Haloperidol-Induced Catalepsy by Noradrenaline and L-Threo- DOPS," *Journal of Neural Transmission. Parkinson's Disease and Dementia Section*, 1993, pp. 17-26, vol. 6. No. 1, Austria.

Yamamoto et al., "Pyridostigmine in Autonomic Failure: Can We Treat Postural Hypotension and Bladder Dysfunction With One Drug?" *Clinical Autonomic Research*, 2006, pp. 296-298, vol. 16, No. 4.

Yoshida et al., "Inhibitory Effects of L-Threo-DOPS on Electroshock Seizure in Mice," *Brain and Nerve*, 1989, pp. 567-573, vol. 41, No. 6, Japan.

Yu et al. "Novel Phenserine-Based-Selective Inhibitors of Butyrylcholinesterase for Alzheimer's Disease." Reprinted with permission from *J. Med. Chem.*, May 20, 1999, 42, 1855-1861.

Yu et al. "Total Syntheses and Anticholinesterase Activities of (3aS)-N (8)-Norphenserine, Their Antipodal Isomers, and Other N (8)-Substituted Analogues." *J. Med. Chem.* (1997) vol. 40, 2895-2901.

Zern et al., "Effect of Increased Pancreatic Islet Norepinephrine, Dopamine and Serotonin Concentration on Insulin Secretion in the Golden Hamster," *Diabetologia*, 1980, pp. 341-346, vol. 18, No. 4, Berlin.

www.merck.com, "Orthostatic Hypotension and Syncope," *The Merck Manual of Diagnosis and Therapy*, 1996, Soc. 16, Chapter 200.

Dadabhoy et al., Therapy Insight: Fibromyalgia—a Different Type of Pain Needing a Different Type of Treatment, *Nature Clinical Practice, Rheumatology*, 2006, pp. 364-372, vol. 2.

Lawson, "Tricyclic Antidepressants and Fibromyalgia: What is the Mechanism of Action?," *Expert Opinion on Investigational Drugs*, 2002, pp. 1437-1445, vol. 12.

Martignoni et al., "Cardiovascular Dysautonomia as a Cause of Falls in Parkinson's Disease," *Parkinsonism and Related Disorders*, 2006, pp. 195-204, vol. 12.

Mease et al., "Fibromyalgia: Should the Treatment Paradigm be Monotherapy or Combination Pharmacotherapy?," *Current Pain and Headache Reports*, 2008, pp. 399-405, vol. 12.

Myllylä et al., Effect of Entacapone, a COMT Inhibitor, on the Pharmacokinetics of Levodopa and on Cardiovascular Responses in Patients with Parkinson's Disease, 1993, *Euro J Clin Pharmacol.*, 1993, pp. 419-423, vol. 45.

Schroeder et al., Norepinephrine Transporter Inhibition Prevents Tilt-Induced Pre-Syncope, *Journal of the American College of Cardiology*, 2006, pp. 516-522, vol. 48, No. 3.

Yunus, "Fibromyalgia and Overlapping Disorders: The Unifying Concept of Central Sensitivity Syndromes," *Semin. Arthritis Rheum.*, 2007, pp. 339-356, vol. 36.

http://web.archive.org/web/20050831044729/http://courses.washington.edu/chat"Catecholamines as Neurotransmitters/Hormones," University of Washington—School of Medicine, Cardiovascular & Autonomic Pharmacology module, Aug. 31, 2005, pp. 1-7.

Garcia-Borreguero et al., "Parkinson's Disease and Sleep," *Sleep Medicine Reviews*, 2003, 7(2), pp. 115-129.

Gilden, "Midodrine in Neurogenic Orthostatic Hypotension. A New Treatment," *International Angiology*, 1998, vol. 17(3), pp. 125-131.

Kaufmann et al., "Midodrine in Neurally Mediated Syncope: A Double-Blind,, Randomized, Crossover Study," *Annals of Neurology*, 2002, vol. 52, pp. 342-345.

* cited by examiner

DROXIDOPA AND PHARMACEUTICAL COMPOSITION THEREOF FOR THE TREATMENT OF MOOD DISORDERS, SLEEP DISORDERS OR ATTENTION DEFICIT DISORDERS

CROSS-REFERENCE TO RELATED APPLICATIONS

The present application claims priority to U.S. Provisional Patent Application No. 60/916,497, filed May 7, 2007, which is incorporated herein by reference in its entirety.

FIELD OF THE INVENTION

The present application is directed to methods of treatment of various conditions. In particular, the application is directed to the use of droxidopa, alone or in combination with one or more additional components, for the treatment of various conditions, such as mood disorders, sleep disorders, or attention deficit disorders.

BACKGROUND

Droxidopa is a known synthetic amino acid precursor of norepinephrine that is converted directly to norepinephrine via the action of dopa decarboxylase (DDC). Droxidopa is generally used to treat orthostatic hypotension (OH) and can be categorized as an antiparkinsonian agent; however, multiple pharmacological activities have been observed with droxidopa, including the following: (1) it is directly converted to 1-norepinephrine by the action of the aromatic L-amino acid decarboxylase which is widely distributed in a living body, and thus has an effect of replenishing norepinephrine; (2) it has limited permeability through the blood-brain barrier into the brain; (3) it specifically recovers norepinephrine activated nerve functions which have decreased in the central and peripheral nervous system; and (4) it shows various actions, as norepinephrine, via the adrenaline receptors in various tissues.

Mood disorders form a category of mental health problems that include all types of depression and are sometimes called affective disorders. The most common types of mood disorders include: major depressive disorder, which is defined as an at least two-week period of a depressed or irritable mood or a noticeable decrease in interest or pleasure in usual activities, along with other signs of a mood disorder; dysthymia (dysthymic disorder), which is defined as a chronic, low-grade, depressed or irritable mood for at least one year; manic depression (bipolar disorder), which is defined as at least one episode of a depressed or irritable mood and at least one period of a manic (persistently elevated) mood; mood disorder due to a general medical condition (such as cancer, injuries, infections, and chronic medical illnesses), which can trigger symptoms of depression; and substance induced mood disorder, wherein symptoms of depression are present due to the effects of medication, drug abuse, exposure to toxins, or other forms of treatment.

Depending upon age and the type of mood disorder present, a person may exhibit different symptoms of depression. The following are the most common symptoms of a mood disorder; however, each individual may experience symptoms differently. Symptoms may include: persistent feelings of sadness; feeling hopeless or helpless; having low self-esteem; feeling inadequate; excessive guilt; feelings of wanting to die; loss of interest in usual activities or activities once enjoyed; difficulty with relationships; sleep disturbances; changes in appetite or weight; decreased energy; difficulty concentrating; a decrease in the ability to make decisions; suicidal thoughts or attempts; frequent physical complaints (i.e., headache, stomach ache, fatigue); running away or threats of running away from home; hypersensitivity to failure or rejection; and irritability, hostility, or aggression. In mood disorders, these feelings appear more intense than what a person may normally feel from time to time, and these feelings tend to continue over a period of time or interfere with an individual's interest in family, friends, community, or work.

Various treatments are currently available for mood disorders. Examples of current treatments include antidepressant medications, psychotherapy, and family therapy. Three major types of medication are typically used to treat depression: tricyclics, selective serotonin re-uptake inhibitors (SSRIs), and monoamine oxidase inhibitors (MAO inhibitors). All three classes of medications are known to have varying degrees of effectiveness from patient to patient. Moreover, all three classes of medications are known to cause varying, undesirable side effects. It is estimated that approximately 44 million Americans experience a mental disorder each year, and mental illnesses are among the most common conditions affecting health today. Accordingly, there remains a need in the art for further pharmaceutical compositions useful in the treatment of mood disorders, particularly depression.

Sleep disorder encompasses a broad range of conditions, including sleep apnea (brief periods while sleeping during which breathing stops), insomnia (which includes difficulty falling asleep or staying asleep, waking too early, or Sleep State Misperception), narcolepsy (an irresistible need to sleep, where sleep attacks lasting from about 30 seconds to about 30 minutes occur during waking hours), and restless leg syndrome (a discomfort in the legs, often sensed while trying to sleep, which can include crawling, tingling, or prickling sensation, that can be relieved by moving or stimulating the legs). Sleep disorders are often comorbid with other conditions, such as depression, fibromyalgia, and chronic fatigue syndrome.

Narcolepsy, in particular, is known to adversely affect an individual's ability to function in daily life. This condition may be classified under the broader term of hypersomnia, which encompasses additional sleep attack conditions, such as idiopathic hypersomnia, recurrent hypersomnia, and hypersomnia resulting from a medical condition. The "sleep attacks" common with narcolepsy can occur at any time, such as while working, carrying on a conversation, or even driving a car. The four classic symptoms of narcolepsy are excessive daytime sleepiness; cataplexy (sudden, brief episodes of muscle weakness or paralysis brought on by strong emotions such as laughter, anger, surprise, or anticipation); sleep paralysis (paralysis upon falling asleep or waking up); and hypnagogic hallucinations (vivid dreamlike images that occur at sleep onset). Disturbed nighttime sleep, including tossing and turning in bed, leg jerks, nightmares, and frequent awakenings, may also occur.

There is no known cure for narcolepsy, but some evidence suggests the condition may be linked to abnormalities in cerebral perfusion. See Joo et al., *Neuroimage* (2005), 28(2): p. 410-416, which is incorporated herein by reference. Excessive daytime sleepiness is typically treated with stimulant drugs, such as methylphenidate (e.g., RITALIN®), dextroamphetamine (e.g., DEXTROSTAT® or DEXEDRINE®), methamphetamine (DESOXYN®), pemoline (CYLERT®), mazindol (SANOREX®), as well as the "non-stimulant" stimulant modafinil (PROVIGIL®). Cataplexy and other REM-sleep symptoms are often treated with antidepressant medications, such as venlafaxine (EFFEXOR®), fluoxetine (PROZAC®), reboxetine (EDRONAX®), imipramine (TOFRANIL®), desipramine (NORPRAMIN® or PERTOFRAN®), protriptyline (TRIPTIL® or VIVACTIL®), and atomoxetine (STRATERRA®). At best, known medications reduce the symptoms, but do not eliminate them entirely. Moreover, such pharmaceutical treatments often have undesirable side effects. Thus, there remains a need in the art for further pharmaceutical compositions useful in the treatment of sleep disorders, particularly narcolepsy.

Insomnia is typically described as difficulty in initiating and/or maintaining sleep, but the term is sometimes used to indicate any and all stages and types of sleep loss. The condition described by the term insomnia can actually encompass multiple types of sleep loss. Sleep onset insomnia (also known as delayed sleep phase syndrome) is a disorder in which the major sleep episode is delayed in relation to the desired clock time of sleep that results in symptoms of sleep onset insomnia or difficulty in awakening at the desired time. Idiopathic insomnia is a long-term (often lifelong) inability to obtain adequate sleep that is presumably due to an abnormality of the neurological control of the sleep-wake system. In such conditions, the insomnia is long-standing, commonly beginning in early childhood, and sometimes existing since birth. Psychophysiological insomnia is a disorder of somatized tension (i.e., conversion of anxiety into physical symptoms) and learned sleep-preventing association that results in a complaint of insomnia and associated decreased functioning during wakefulness.

Treatment for insomnia can vary depending upon the particular patient's needs. Most medications for treating insomnia are sedatives (i.e., hypnotics) or other sleep-inducing drugs, such as muscle relaxers and CNS depressants. Over-the-counter sleep aids typically include antihistamines (e.g., diphenhydramine or doxylamine), which have the side effect of causing sleepiness. Examples of prescription sleep aids include zolpidem (AMBIEN®), zalepon (SONATA®), and eszopiclone (LUNESTA®). Such medications are generally prescribed (or suggested in relation to OTC drugs) for short term use only. In the absence of drug treatment, several methods for inducing sleep have also been suggested. Methods used for treatment include behavioral modification, following good sleep hygiene practices, and light therapy.

Attention deficit disorder is officially recognized by the American Psychiatric Association as Attention-Deficit/Hyperactivity Disorder, or AD/HD, although most lay people, and even some professionals, still use the separate terms Attention Deficit Disorder (ADD) or Attention Deficit Hyperactivity Disorder (ADHD). Many researchers believe AD/HD is properly divided into three subtypes according to the main features associated with the disorder: inattentiveness, impulsivity, and hyperactivity. The three subtypes are: AD/HD Predominantly Combined Type; AD/HD Predominantly Inattentive Type; and AD/HD Predominantly Hyperactive-Impulsive Type.

The three subtypes take into account that some patients with AD/HD have little or no trouble sitting still or inhibiting behavior, but may be predominantly inattentive and, as a result, have great difficulty getting or staying focused on a task or activity. Others with AD/HD may be able to pay attention to a task but lose focus because they may be predominantly hyperactive-impulsive and, thus, have trouble controlling impulse and activity. The most prevalent subtype is the Combined Type, and patients with this subtype have significant symptoms of all three characteristics AD/HD is a neurobiologically-based developmental disability, but there is currently no known specific cause for the condition. Some evidence suggests that the disorder is genetically transmitted in many cases and results from a chemical imbalance or deficiency in certain neurotransmitters. Other evidence suggests that AD/HD is partially a result of hypoperfusion of specific regions of the brain (e.g., a result of low regional cerebral blood flow). See Lou, Henriksen, and Bruhn, *Archives of Neurology* (1984), 41(8), which is incorporated herein by reference. Professionals who diagnose AD/HD use the diagnostic criteria set forth by the American Psychiatric Association (1994) in the Diagnostic and Statistical Manual of Mental Disorders; the fourth edition of this manual, known as the DSM-IV, was released in May 1994. The criteria in the DSM-IV, and other essential diagnostic features, are the signs of AD/HD. The primary features associated with the disability are inattention, hyperactivity, and impulsivity.

A patient with AD/HD is usually described as having a short attention span and as being distractible, distractibility and inattentiveness being non-synonymous. Distractibility refers to the short attention span and the ease with which some patients can be pulled off-task. Attention, on the other hand, is a process that has different parts, including focus (picking something on which to pay attention), selection (picking something that needs attention at that moment), and sustaining (paying attention for as long as needed). Attention also includes resistance (avoiding things that remove attention from where it needs to be) and shifting (moving attention to something else when needed). Symptoms of inattention, as listed in the DSM-IV, include: often failing to give close attention to details or making careless mistakes in schoolwork, work, or other activities; often having difficulty sustaining attention in tasks or play activities; often not seeming to listen when spoken to directly; often not following through on instructions and failing to finish schoolwork, chores, or duties in the workplace (not due to oppositional behavior or failure to understand instructions); often having difficulty organizing tasks and activities; often avoiding, disliking, or being reluctant to engage in tasks that require sustained mental effort (such as schoolwork or homework); often losing things necessary for tasks or activities (e.g., toys, school assignments, pencils, books, or tools); often being easily distracted by extraneous stimuli; and often being forgetful in daily activities.

Excessive activity is the most visible sign of AD/HD. Symptoms of hyperactivity, as listed in the DSM-IV, include: often fidgeting with hands or feet or squirming in seat; often leaving seat in classroom or in other situations in which remaining seated is expected; often running about or climbing excessively in situations in which it is inappropriate (in adolescents or adults, may be limited to subjective feelings of restlessness); often having difficulty playing or engaging in leisure activities quietly; often being "on the go" or often acting as if "driven by a motor;" and often talking excessively.

Impulsivity of patients with AD/HD typically encompasses acting before thinking, because they have difficulty waiting or delaying gratification. The impulsivity leads these patients to speak out of turn, interrupt others, and engage in what looks like risk-taking behavior. A child may run across the street without looking or climb to the top of very tall trees. Although such behavior is risky, the patient is not really a risk-taker but, rather, has great difficulty controlling impulse. Symptoms of impulsivity, as listed in the DSM-IV, include: often blurting out answers before questions have been completed; often having difficulty awaiting turn; and often interrupting or intruding on others.

Many medications are approved for use in the treatment of AD/HD; however, stimulants, such as methylphenidate (e.g., RITALIN®) and dextroamphetamine (e.g., DEXTROSTAT® or DEXEDRINE®), are generally recognized as being the most effective pharmaceutical treatment. Other pharmaceutical treatments include atomoxetine (STRATTERA®), bupropion (WELLBUTRIN®), and alpha-2-agonists, such as clonidine (CATAPRES®). AD/HD is most prevalent in children, and many parents find it undesirable to treat their children through administering stimulants. Moreover, there can be undesirable side effects, such as decreased appetite, insomnia, increased anxiety, and/or irritability. Accordingly, there remains a need in the art for further pharmaceutical compositions useful in the treatment of AD/HD.

SUMMARY OF THE INVENTION

The present invention provides pharmaceutical compositions useful in the treatment of various conditions or disorders. The pharmaceutical compositions generally comprise droxidopa alone or in combination with one or more further pharmaceutically active compounds. The invention further provides methods of treating a variety of conditions or disorders. For example, in one aspect, the invention is directed to a method of treating a condition comprising administering to a subject in need of treatment of the condition a pharmaceutical composition comprising a therapeutically effective amount of droxidopa or a pharmaceutically acceptable ester, amide, salt, solvate, prodrug, or isomer thereof, wherein the condition is selected from the group consisting of a mood disorder, a sleep disorder, or an attention deficit disorder.

In one embodiment, the method of the invention comprises treating a mood disorder, particularly depression. Although the word depression alone may be used herein to describe a condition treated by the invention, it is understood that depression is intended to refer to the diagnosed condition of major depressive disorder, such as defined above. In further embodiments, other mood disorders may also be treated, such as dysthymia (dysthymic disorder), manic depression (bipolar disorder), mood disorder due to a general medical condition (such as cancer, injuries, infections, and chronic medical illnesses), and substance induced mood disorder.

The methods of the invention may particularly be characterized as being effective in relation to a specific symptom of the mood disorder. For example, when the mood disorder is depression and the subject is suffering from at least one symptom of depression, the invention can be characterized as eliminating the symptom, reducing the severity of the symptom, or reducing the frequency of occurrence of the symptom. Moreover, administration of an effective amount of a pharmaceutical composition according to the invention may be characterized as an amount effective to achieve the same goal of eliminating or reducing the severity or frequency of a symptom.

In other embodiments, the method of the invention comprises treating a sleep disorder. For example, the method can comprise treating a condition of hypersomnia, particularly narcolepsy. In further embodiments, the sleep disorder treated according to the invention may include insomnia. In particular embodiments, administration of an effective amount of a pharmaceutical composition according to the invention may be characterized as an amount effective to prevent the evident symptom of the sleep disorder (e.g., to prevent narcoleptic events, or related events, during waking hours or prevent insomnia during sleeping hours).

In still further embodiments, the method of the invention comprises treating an attention deficit disorder. In specific embodiments, the attention deficit disorder comprises a condition classified under the title of Attention-Deficit/Hyperactivity Disorder (AD/HD). As before, the methods of the invention may particularly be characterized as being effective in relation to a specific symptom of the attention deficit disorder. For example, when the attention deficit disorder is AD/HD and the subject is suffering from at least one symptom of AD/HD, the invention can be characterized as eliminating the symptom, reducing the severity of the symptom, or reducing the frequency of occurrence of the symptom. Moreover, administration of an effective amount of a pharmaceutical combination according to the invention may be characterized as an amount effective to achieve the same goal of eliminating or reducing the severity or frequency of a symptom.

The methods of the invention can include administration of droxidopa alone or can include administration of droxidopa in combination with one or more further active agents. Accordingly, the invention provides for the administration of a variety of pharmaceutical compositions. In certain embodiments, the additional active agents useful in combination with droxidopa can be selected from the group consisting of DOPA decarboxylase inhibiting compounds, catechol-O-methyltransferase inhibiting compounds, cholinesterase inhibiting compounds, monoamine oxidase inhibiting compounds, norepinephrine reuptake inhibiting compounds, selective serotonin reuptake inhibiting compounds, tricyclic antidepressant compounds, serotonin norepinephrine reuptake inhibiting compounds, norepinephrine dopamine reuptake inhibiting compound, noradrenergic and specific serotonergic antidepressants, and combinations thereof.

In one embodiment, a pharmaceutical composition for use according to the invention comprises droxidopa and a DOPA decarboxylase inhibiting compound. In particular, the DOPA decarboxylase inhibiting compound may selected from the group consisting of benserazide, carbidopa, difluoromethyldopa, α-methyldopa, and combinations thereof.

In another embodiment, a pharmaceutical composition for use according to the invention comprises droxidopa and a catechol-O-methyltransferase inhibiting compound. In particular, the catechol-O-methyltransferase inhibiting compound may be selected from the group consisting of entacapone, tolcapone, nitecapone, and combinations thereof.

In yet another embodiment, a pharmaceutical composition for use according to the invention comprises droxidopa and a cholinesterase inhibiting compound. In particular, the cholinesterase inhibiting compound may be selected from the group consisting of pyridostigmine, donepezil, rivastigmine, galantamine, tacrine, neostigmine, metrifonate, physostigmine, ambenonium, demarcarium, thiaphysovenine, phenserine, edrophonium, cymserine and combinations thereof.

In still another embodiment, a pharmaceutical composition for use according to the invention comprises droxidopa and a monoamine oxidase inhibiting compound. In particular, the monoamine oxidase inhibiting compound may be selected from the group consisting of isocarboxazid, moclobemide, phenelzine, tranylcypromine, selegiline, nialamide, iproniazid, iproclozide, toloxatone, harmala, brofaromine, benmoxin, 5-methoxy-N,N-dimethyltryptamine, 5-methoxy-α-methyltryptamine, and combinations thereof.

In a further embodiment, a pharmaceutical composition for use according to the invention comprises droxidopa and a norepinephrine reuptake inhibiting compound. In particular, the norepinephrine reuptake inhibiting compound may be selected from the group consisting of atomoxetine, reboxetine, viloxazine, maprotiline, bupropion, radafaxine, and combinations thereof.

In yet a further embodiment, a pharmaceutical composition for use according to the invention comprises droxidopa and a selective serotonin reuptake inhibiting compound. In particular, the selective serotonin reuptake inhibiting compound may be selected from the group consisting of fluoxetine, paroxetine, citalopram, escitalopram, fluvoxamine, sertraline, and combinations thereof.

In still another embodiment, a pharmaceutical composition for use according to the invention comprises droxidopa and a tricyclic antidepressant compound. In particular, the tricyclic antidepressant compound may selected from the group consisting of amitriptyline, amoxapine, butriptyline, clomipramine, desipramine, dibenzepin, dosulepin, doxepin, imipramine, lofepramine, nortriptyline, protriptyline, trimipramine, and combinations thereof.

In a particular embodiment, a pharmaceutical composition for use according to the invention comprises droxidopa, a tricyclic antidepressant, and a DOPA decarboxylase inhibiting compound.

When the droxidopa is combined with one or more additional active agents, the co-administration can be via a variety of methods. For example, the droxidopa and the additional active agent can be in the same pharmaceutical composition. In other embodiments, the droxidopa and the additional active agent can be administered in separate compositions. In such embodiments, the separated compositions can be administered at the same time or within close proximity to one another. Alternatively, the separate compositions can be administered as different times, which may be desirable to optimize the effects of the co-administered active agents.

In another aspect, the invention is specifically directed to pharmaceutical compositions comprising novel combinations of active agents. In certain embodiments, a pharmaceutical composition according to the invention comprises droxidopa and a tricyclic antidepressant compound. In further embodiments, the composition may further comprise a compound selected from the group consisting of DOPA decarboxylase inhibiting compounds, catechol-O-methyltransferase inhibiting compounds, cholinesterase inhibiting compounds, monoamine oxidase inhibiting compounds, norepinephrine reuptake inhibiting compounds, selective serotonin reuptake inhibiting compounds, tricyclic antidepressant compounds, serotonin norepinephrine reuptake inhibiting compounds, norepinephrine dopamine reuptake inhibiting compound, noradrenergic and specific serotonergic antidepressants, and combinations thereof. In a particular embodiment, a pharmaceutical composition according to the invention comprises: droxidopa; a tricyclic antidepressant compound; and a DOPA decarboxylase inhibiting compound.

In still another aspect, the present invention is directed to methods of treating conditions that have at least one underlying cause related to hypoperfusion of the brain (i.e., reduced blood flow to an area of the brain). One example of hypoperfusion is reduced cerebral blood flow.

In one embodiment, the invention is directed to a method of treating a patient suffering from a condition at least partially arising from reduced blood flow in the brain, the method comprising administering to the patient an amount of droxidopa that is therapeutically effective to increase brain blood flow and thus treat the condition. In specific embodiments, the condition may particularly be selected from the group of mood disorders, sleep disorders, and attention deficit disorders.

In carrying the method according to this aspect of the invention, the droxidopa may be combined with one or more additional active agents. In some embodiments, the additional active agent may be selected from the group consisting of DOPA decarboxylase inhibiting compounds, catechol-O-methyltransferase inhibiting compounds, cholinesterase inhibiting compounds, monoamine oxidase inhibiting compounds, norepinephrine reuptake inhibiting compounds, selective serotonin reuptake inhibiting compounds, tricyclic antidepressant compounds, serotonin norepinephrine reuptake inhibiting compounds, norepinephrine dopamine reuptake inhibiting compound, noradrenergic and specific serotonergic antidepressants, and combinations thereof.

BRIEF DESCRIPTION OF THE DRAWINGS

Figure 1:
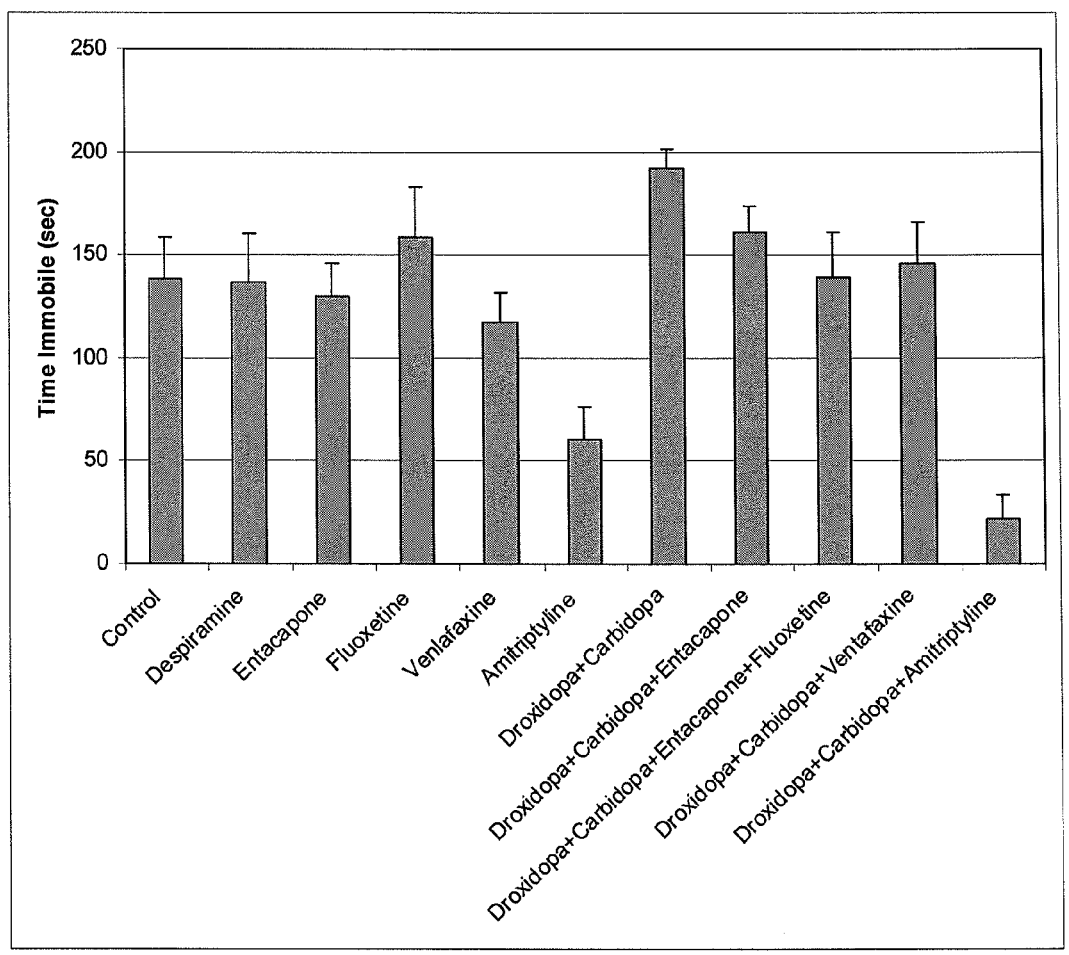
Figure 2:
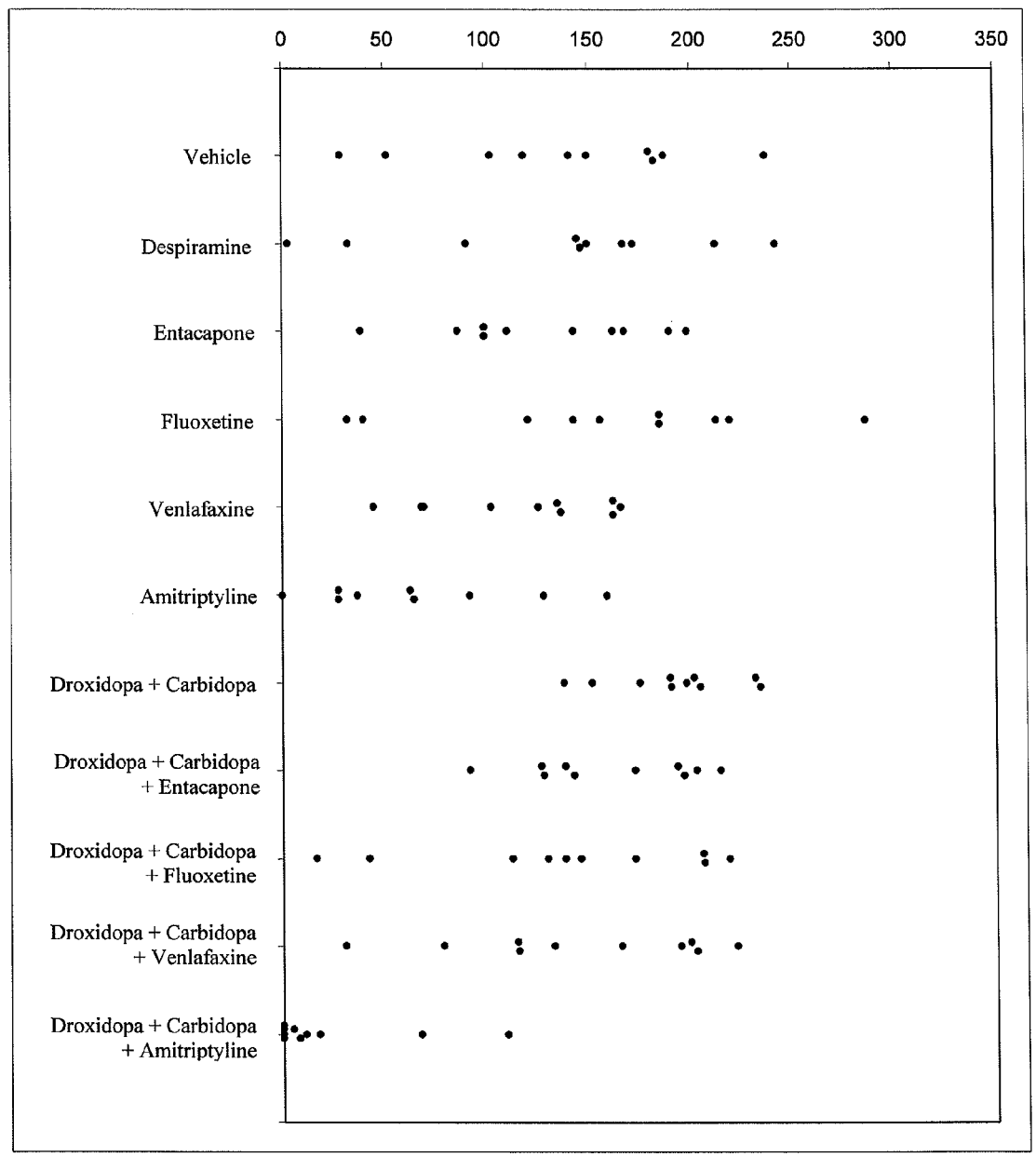

Having thus described the invention in general terms, reference will now be made to the accompanying drawings wherein:

FIG. 1 is a graph illustrating average time immobile for 11 groups of mice (10 in each group) treated with 11 different compositions and evaluated in a murine Forced Swim Test, to determine the antidepressive effects of the compositions; and FIG. 2 is a chart illustrating the actual data points on the time immobile scale for all mice evaluated in the murine Forced Swim Test.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides pharmaceutical compositions and methods that can be used in the treatment of a variety of disorders that can find a basis in regulating CNS activity and, thus, may include a certain level of interconnectivity. In particular, the compositions and methods can be used in the treatment of mood disorders, sleep disorders, and attention deficit disorders. Treatment can comprise the use of droxidopa as a single active agent. In other embodiments, treatment can comprise the use of droxidopa in combination with one or more further active agents. Examples of such combinations are disclosed in U.S. Patent Application Publication 2008/0015181, which is incorporated herein by reference in its entirety. The specific pharmaceutical composition (or compositions) used in the invention, and the methods of treatment provided by the invention, are further described below.

I. Definitions

The term "alkyl" as used herein means saturated straight, branched, or cyclic hydrocarbon groups. In particular embodiments, alkyl refers to groups comprising 1 to 10 carbon atoms ("$C_{1-10}$ alkyl"). In further embodiments, alkyl refers to groups comprising 1 to 8 carbon atoms ("$C_{1-8}$ alkyl"), 1 to 6 carbon atoms ("$C_{1-6}$ alkyl"), or 1 to 4 carbon atoms ("$C_{1-4}$ alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. Substituted alkyl refers to alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "heteroalkyl" as used herein means alkyl moieties wherein at least one C atom is replaced with a non-carbon atom, such as N, O, or S.

The term "alkenyl" as used herein means alkyl moieties wherein at least one saturated C—C bond is replaced by a double bond. In particular embodiments, alkenyl refers to groups comprising 1 to 10 carbon atoms ("$C_{1-10}$ alkenyl"). In further embodiments, alkyl refers to groups comprising 1 to 8 carbon atoms ("$C_{1-8}$ alkenyl"), 1 to 6 carbon atoms ("$C_{1-6}$ alkenyl"), or 1 to 4 carbon atoms ("$C_{1-4}$ alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "heteroalkenyl" as used herein means alkenyl moieties wherein at least one C atom is replaced with a non-carbon atom, such as N, O, or S.

The term "alkynyl" as used herein means alkyl moieties wherein at least one saturated C—C bond is replaced by a triple bond. In particular embodiments, alkynyl refers to groups comprising 1 to 10 carbon atoms ("$C_{1-10}$ alkynyl"). In further embodiments, alkyl refers to groups comprising 1 to 8 carbon atoms ("$C_{1-8}$ alkynyl"), 1 to 6 carbon atoms ("$C_{1-6}$ alkynyl"), or 1 to 4 carbon atoms ("$C_{1-4}$ alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "heteroalkynyl" as used herein means alkynyl moieties wherein at least one C atom is replaced with a non-carbon atom, such as N, O, or S.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("$C_{1-10}$ alkoxy"). In further embodiments, alkoxy refers to oxygen-linked groups comprising 1 to 8 carbon atoms ("$C_{1-8}$ alkoxy"), 1 to 6 carbon atoms ("$C_{1-6}$ alkoxy"), or 1 to 4 carbon atoms ("$C_{1-4}$ alkoxy").

The term "halo" or "halogen" as used herein means fluorine, chlorine, bromine, or iodine.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl, naphthyl, tetrahydronaphthyl, and biphenyl. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined above.

The term "acyl" as used herein means a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, $C_1$-$C_6$ alkyl or $C_1$-$C_6$ alkoxy; sulfonate esters such as alkyl or aralkyl sulphonyl including methanesulfonyl; mono-, di-, or triphosphate ester; trityl or monomethoxytrityl; substituted benzyl; trialkylsilyl such as dimethyl-t-butylsilyl or diphenylmethylsilyl. Aryl groups in the esters optimally comprise a phenyl group.

The term "amino" as used herein means a moiety represented by the structure $NR_2$, and includes primary amines, and secondary and tertiary amines substituted by alkyl (i.e., alkylamino). Thus, $R_2$ may represent two hydrogen atoms, two alkyl moieties, or one hydrogen atom and one alkyl moiety.

The terms "alkylamino" and "arylamino" as used herein mean an amino group that has one or two alkyl or aryl substituents, respectively.

The term "hydroxyalkyl" as used herein means an alkyl group as described above including one or more hydroxy groups thereon.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

II. Active Agents

The present invention provides pharmaceutical compositions and methods of treatment of various conditions using such pharmaceutical compositions. The pharmaceutical compositions of the invention generally comprise droxidopa as an active agent. In certain embodiments, the pharmaceutical compositions can comprise one or more further active agents.

A. Droxidopa

The compositions for use in the methods of the invention generally comprise, as an active ingredient, threo-3-(3,4-dihydroxyphenyl)serine, which is commonly known as droxidopa and has the structure provided below in Formula (1).

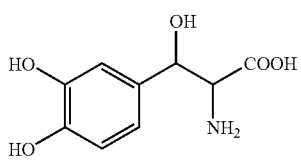
(1)

Droxidopa is also known as threo-β,3-dihydroxy-L-tyrosine, (−)-(2S,3R)-2-amino-3-hydroxy-3-(3,4-dihydroxyphenyl) propionic acid, and threo-dopaserine, as well as the common terms DOPS, threo-DOPS, and L-DOPS. The compound can is optically active and can be provided in various forms, including L-threo-DOPS, D-threo-DOPS, L-erythro-DOPS, and D-erythro-DOPS. The compounds can also exist in the racemic form. The L-threo isomer is generally preferred according to the present invention; however, the invention also encompasses compositions and methods of use incorporating the other forms of droxidopa. Accordingly, as used throughout the present disclosure, the term "droxidopa" is intended to encompass any isolated or purified isomer (e.g., the L-threo isomer), as well as the racemic forms of droxidopa.

Droxidopa useful according to the invention can be prepared by a variety of conventional methods, including methods particularly useful for isolating the L-isomer of droxidopa. See, for example, U.S. Pat. No. 3,920,728; U.S. Pat. No. 4,319,040; U.S. Pat. No. 4,480,109; U.S. Pat. No. 4,562,263; U.S. Pat. No. 4,699,879; U.S. Pat. No. 5,739,387; and U.S. Pat. No. 5,864,041, which are incorporated herein by reference.

The present invention also encompasses compositions comprising one or more pharmaceutically acceptable esters, amides, salts, solvates, prodrugs, or isomers of droxidopa. In one embodiment, the invention involves use of droxidopa esters that allow for slowed or delayed decarboxylation of droxidopa resulting from hydrolytic or enzymatic degradation of the ester linkage. As would be recognized by one of skill in the art, an ester of droxidopa can be formed by replacing the hydrogen on the carboxylic ester group with any suitable ester-forming group. For example, U.S. Pat. No. 5,288,898, which is incorporated herein by reference, discloses various esters of N-methylphenylserine, including methyl esters, ethyl esters, n-propyl esters, isopropyl esters, n-butyl esters, isobutyl esters, tert-butyl esters, n-pentyl esters, isopentyl esters, n-hexyl esters, and the like, and the present invention encompasses such esters, as well as other esters. Further examples of ester-forming groups that could be used according to the invention are disclosed in U.S. Pat. No. 5,864,041, which is incorporated herein by reference in its entirety. Accordingly, the compounds of the present invention particularly encompass a droxidopa ester, including esters that are N-substituted and esters that are not N-substituted.

B. Additional Active Agents

As noted above, in certain embodiments, the compositions for use according to the methods of the invention can comprise one or more active agents in addition to droxidopa. Various preferred active agents that can be combined with droxidopa for treatment of the conditions noted herein are described below. Of course, such disclosure should not be viewed as limiting the scope of further active agents that may be combined with droxidopa. Rather, further active compounds, particularly compounds identified as useful for treating mood disorders, sleep disorders, or attention deficit disorders, or for treating, preventing, or ameliorating symptoms associated with such disorders, may be used in addition to the compounds specifically disclosed herein.

In one particular embodiment, an active agent used in combination with droxidopa comprises one or more DOPA decarboxylase (DDC) inhibiting compounds. DDC catalyzes the decarboxylation of levodopa (L-DOPA or 3,4-dihydroxy-L-phenylalanine) and 5-hydroxytryptophan (5-HTP) to yield dopamine and serotonin, respectively. Similarly, DDC catalyzes the conversion of droxidopa to norepinephrine. DDC inhibiting compounds prevent the above-noted conversions and are useful in combination with precursor drugs (such as droxidopa) to focus conversion within the central nervous system and thus increase the concentration of droxidopa in the CNS.

Any compound typically recognized as inhibiting or decreasing the activity of DDC can be used according to the present invention. Non-limiting examples of DDC inhibiting compounds useful according to the invention comprise benserazide, carbidopa, difluoromethyldopa, α-methyldopa, and combinations thereof.

In further embodiments, an active agent used in combination with droxidopa comprises one or more compounds that at least partially inhibit the function of catechol-O-methyltransferase (such compounds being generally referred to as "COMT inhibiting compounds"). Catechol-O-methyltransferase catalyzes the transfer of the methyl group from S-adenosyl-L-methionine to various catechol compounds (e.g., catecholamines), including dopamine, epinephrine, norepinephrine, and droxidopa. The COMT enzyme is important in the extraneuronal inactivation of catecholamines and drugs with catechol structures, and is generally one of the most important enzymes involved in the metabolism of catecholamines and their metabolites. It is present in most tissues, including the peripheral and the central nervous system.

Inhibitors of COMT slow metabolism and elimination of catechol compounds by increasing their half-life. Accordingly, COMT inhibiting compounds can function to increase levels of naturally occurring catechol compounds, as well as alter the pharmacokinetics of administered catechol compounds (such as L-β-3,4-dihydroxyphenylalanine (L-DOPA), an immediate precursor of dopamine, generally used for symptomatic treatment of Parkinson's disease). Inhibitors of COMT can act peripherally (such as the compound entacapone), while others (such as tolcapone) are capable of crossing the blood-brain barrier and thus acting centrally and peripherally.

Any compound generally recognized as being a COMT inhibitor can be used as an additional active agent according to the invention. Non-limiting examples of COMT inhibiting compounds useful in combination with droxidopa according to the invention include the following: [(E)-2-cyano-N,N-diethyl-3-(3,4-dihydroxy-5-nitrophenyl)propenamide], also called entacapone (COMTAN®); 4-dihydroxy-4'-methyl-5-nitrobenzophenone, also called tolcapone (TASMAR®); and 3-(3,4-dihydroxy-5-nitrophenyl)methylene-2,4-pentanedione, also called nitecapone. In addition to the above examples, U.S. Pat. No. 6,512,136 (the disclosure of which is incorporated herein by reference) describes various substituted 2-phenyl-1-(3,4-dihydroxy-5-nitrophenyl)-1-ethanone compounds that may also be useful as COMT inhibitors according to the present invention. Likewise, U.S. Pat. No. 4,963,590; GB 2 200 109; U.S. Pat. No. 6,150,412; and EP 237 929, each describes groups of COMT inhibiting compounds that could be useful according to the present invention, and the disclosure of each of the above-noted documents is incorporated herein by reference.

According to another embodiment of the invention, an active agent used in combination with droxidopa comprises one or more compounds that at least partially inhibit the function of cholinesterase. Such cholinesterase inhibiting compounds may also be referred to as anticholinesterase compounds. Cholinesterase inhibiting compounds can be reversible or non-reversible. The present invention preferably encompasses any compounds that may be considered reversible cholinesterase inhibiting compounds (either competitive or non-competitive inhibitors). Non-reversible cholinesterase inhibitors generally find use as pesticides (such as diazinon and Sevin) and chemical weapons (such as tabin and sarin) and are not preferred according to the present invention.

Cholinesterase inhibitors are understood to include compounds that increase levels of acetylcholine (or a cholinergic agonist), generally by reducing or preventing the activity of chemicals involved in the breakdown of acetylcholine, such as acetylcholinesterase. Cholinesterase inhibitors may also include compounds having other mechanisms of action, such as stimulating release of acetylcholine, enhancing response of acetylcholine receptors, or potentiating gonadotropin releasing hormone (GNRH)-induced growth hormone release. Moreover, cholinesterase inhibiting compounds may act by enhancing ganglionic transmission.

Any compound generally recognized as being a cholinesterase inhibitor (or an anticholinesterase compound) may be useful according to the present invention. Non-limiting examples of cholinesterase inhibiting compounds useful in combination with droxidopa for preparing compositions according to the invention include the following: 3-dimethylcarbamoyloxy-1-methylpyridinium, also called pyridostigmine (MESTINON® or Regonol); (±)-2,3-dihydro-5,6-dimethoxy-2-[[1-(phenylmethyl)-4-piperidinyl]methyl]-1H-inden-1-one, also called donepezil (ARICEPT®); (S)—N-ethyl-3-((1-dimethyl-amino)ethyl)-N-methylphenyl-carbamate, also called rivastigmine (Exelon); (4aS,6R,8aS)-4a,5,9,10,11,12-hexahydro-3-methoxy-11-methyl-6H-benzofuro[3a,3,2ef][2]benzazepin-6-ol, also called galantamine (REMINYL® or RAZADYNE®); 9-amino-1,2,3,4-tetrahydroacridine, also called tacrine (COGNEX®); (m-hydroxyphenyl) trimethylammonium methylsulfate dimethylcarbamate, also called neostigmine; 1-hydroxy-2,2,2-trichloroethylphosphonic acid dimethyl ester, also called metrifonate or trichlorofon; 1,2,3,3A,8,8A-hexahydro-1,3a,8-trimethylpyrrolo-[2,3-b]-indole-5-ol methylcarbamate ester, also called physostigmine; [Oxalylbis(iminoethylene)]-bis-[(o-chlorobenzyl)diethylammonium]dichloride, also called ambenonium (MYTELASE®); ethyl (m-hydroxyphenyl) dimethylammonium, also called edrophonium (ENLON®); demarcarium; thiaphysovenine; phenserine; and cymserine.

More generally, compounds useful as cholinesterase inhibitors according to the invention can comprise carbamate compounds, particularly phenylcarbamates, oganophosphate compounds, piperidines, and phenanthrine derivatives. The invention further comprises cholinesterase inhibitors that are carbamoyl esters, as disclosed in U.S. Published Patent Application No. 2005/0096387, which is incorporated herein by reference.

The above groups of compounds, and specific compounds, are provided to exemplify the types of cholinesterase inhibiting compounds that are useful according to the invention and should not be viewed as limiting the scope of the invention. In fact, the invention can incorporate various further cholinesterase inhibitors, including compounds described in the following documents, the disclosures of which are incorporated herein by reference: Brzostowska, Malgorzata, et al. "Phenylcarbamates of (−)-Eseroline, (−)-N1-Noreseroline and (−)-Physovenol: Selective Inhibitors of Acetyl and, or Butyrylcholinesterase." *Medical Chemistry Research.* (1992) Vol. 2, 238-246; Flippen-Anderson, Judith L., et al. "Thiaphysovenol Phenylcarbamates: X-ray Structures of Biologically Active and Inactive Anticholinesterase Agents." *Heterocycles.* (1993) Vol. 36, No. 1; Greig, Nigel H., et al. "Phenserine and Ring C Hetero-Analogues: Drug Candidates for the Treatment of Alzheimer's Disease." *Medicinal Research Reviews.* (1995) Vol. 15, No. 1, 3-31; He, Xiao-shu, et al. "Thiaphysovenine and Carbamate Analogues: A New Class of Potent Inhibitors of Cholinesterases." *Medical Chemistry Research.* (1992) Vol. 2, 229-237; Lahiri, D. K., et al. "Cholinesterase Inhibitors, β-Amyloid Precursor Protein and Amyloid β-Peptides in Alzheimer's Disease." *Acta Neurologica Scandinavia.* (December 2000) Vol. 102 (s176), 60-67; Pei, Xue-Feng, et al. "Total Synthesis of Racemic and Optically Active Compounds Related to Physostigimine and Ring-C Heteroanalogues from 3-[-2'-(Dimethylamino0ethyl]-2,3-dihydro-5-methoxy-1,3-dimethyl-1H-indol-2-ol." *Helvetica Chimica ACTA.* (1994) Vol. 77; Yu, Qian-sheng, et al. "Total Syntheses and Anticholinesterase Activities of (3aS)-N (8)-Norphysostigmine, (3aS)-N (8)-Norphenserine, Their Antipodal Isomers, and Other N (8)-Substituted Analogues." *J. Med. Chem.*, (1997) Vol. 40, 2895-2901; and Yu, Q. S., et al. "Novel Phenserine-Based-Selective Inhibitors of Butyrylcholinesterase for Alzheimer's Disease." Reprinted with permission from *J. Med. Chem.*, May 20, 1999, 42, 1855-1861.

An active agent used in combination with droxidopa according to the invention can particularly be chosen from the group of compounds recognized as antidepressant compounds. As used herein, an antidepressant can refer to any psychiatric medication or other substance (including nutrients and herbs) used for treating a mood disorder, particularly depression and/or dysthymia. Non-limiting examples of antidepressants according to the invention include monoamine oxidase inhibitors (MAOIs), norepinephrine reuptake inhibitors (NRIs), selective serotonin reuptake inhibitors (SSRIs), tricyclic antidepressant compounds, serotonin norepinephrine reuptake inhibitors (SNRIs, also known as 5-HT-NE dual reuptake inhibitors), norepinephrine dopamine reuptake inhibitors (NDRIs), and noradrenergic and specific serotonergic antidepressants (NASSAs).

According to yet another embodiment of the invention, an active agent used in combination with droxidopa comprises one or more compounds that at least partially inhibit the function of monoamine oxidase. Monoamine oxidase inhibitors (MAOIs) comprise a class of compounds understood to act by inhibiting the activity of monoamine oxidase, an enzyme generally found in the brain and liver of the human body, which functions to break down monoamine compounds, typically through deamination.

There are two isoforms of monoamine oxidase inhibiting compounds, MAO-A and MAO-B. The MAO-A isoform preferentially deaminates monoamines typically occurring as neurotransmitters (e.g., serotonin, melatonin, epinephrine, norepinephrine, and dopamine). Thus, MAOIs have been historically prescribed as antidepressants and for treatment of other social disorders, such as agoraphobia and social anxiety. The MAO-β isoform preferentially deaminates phenylethylamine and trace amines. Dopamine is equally deaminated by both isoforms. MAOIs may by reversible or non-reversible and may be selective for a specific isoform. For example, the MAOI moclobemide (also known as Manerix or Aurorix) is known to be approximately three times more selective for MAO-A than MAO-B.

Any compound generally recognized as being an MAOI may be useful according to the present invention. Non-limiting examples of MAOIs useful in combination with droxidopa for preparing compositions according to the invention include the following: isocarboxazid (MARPLAN®); moclobemide (Aurorix, Manerix, or Moclodura); phenelzine (NARDIL®); tranylcypromine (PARNATE®); selegiline (ELDEPRYL®, EMSAM®, or l-deprenyl); lazabemide; nialamide; iproniazid (marsilid, iprozid, ipronid, rivivol, or propilniazida); iproclozide; toloxatone; harmala; brofaromine (Consonar); benmoxin (Neuralex); and certain tryptamines, such as 5-MeO-DMT (5-Methoxy-N,N-dimethyltryptamine) or 5-MeO-AMT (5-methoxy-α-methyltryptamine).

According to still another embodiment of the invention, an active agent used in combination with droxidopa comprises one or more norepinephrine reuptake inhibiting compounds (NRI). NRIs are also known or noradrenalin reuptake inhibitors (NARI) and generally function to elevate the level of norepinephrine in the central nervous system (CNS) by inhibiting reuptake of norepinephrine from the synaptic cleft into the presynaptic neuronal terminal. Norepinephrine is a catecholamine and phenylethylamine that functions as a neurotransmitter and is known to affect many conditions.

Any compound typically recognized as inhibiting the reuptake of norepinephrine in the CNS can be used according to the present invention. Non-limiting examples of NRIs useful according to the invention comprise atomoxetine (STRATTERA®), reboxetine (EDRONAX®, VESTRA®, or NOREBOX®), viloxazine (EMOVIT®, VIVALAN®, VIVARINT®, or VIVILAN®), maprotiline (DEPRILEPT®, LUDIOMIL®, or PSYMION®), bupropion (WELLBUTRIN® or ZYBAN®), and radafaxine. Note that bupropion may also be classified as a norepinephrine dopamine reuptake inhibitor, as described below.

In yet another embodiment, an active agent used in combination with droxidopa comprises one or more selective serotonin reuptake inhibiting compounds (SSRIs). Non-limiting examples of specific SSRIs useful according to the invention comprise fluoxetine (PROZAC®), paroxetine (PAXIL®), citalopram (CELEXA®), escitalopram (LEXAPRO®), fluvoxamine (LUVOX®), and sertraline (ZOLOFT®).

In certain embodiments of the invention, droxidopa may be combined with one or more compounds recognized as being a tricyclic antidepressant. Tricyclic antidepressants (TCA) are a class of antidepressant compounds that can be described as including any compound exhibiting antidepressant activity and having a chemical formula including a fused three ring structure. In certain embodiments, a tricyclic antidepressant for combination with droxidopa (and optionally one or more further compounds) comprises a compound having the structure of Formula (2),

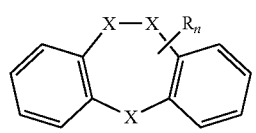

(2)

wherein X is C, N, O, or S; R is a substituent present on one, two, or all three non-fused atoms of the central ring (each substituent being independent of the other) and is selected from the group of H, carbonyl, halo, amino, optionally substituted alkyl or heteroalkyl, optionally substituted alkenyl or heteroalkenyl, optionally substituted alkynyl or heteroalkynyl, or optionally substituted alkaryl or aralkyl, wherein the optional substituent is selected from alkyl, alkenyl, alkynyl, hydroxyalkyl, and optionally substituted aryl; and n is an integer from 0 to 6.

In certain embodiments, a tricyclic antidepressant for use according to the present invention is selected from the group consisting of amitriptyline (ELAVIL®), amoxapine, butriptyline, clomipramine (ANAFRANIL®), desipramine (NORPRAMIN®), dibenzepin, dosulepin, doxepin (SINEQUAN®), imipramine (TOFRANIL®), lofepramine, nortriptyline (PAMELOR® or AVENTYL®), protriptyline (VIVACTYL®), trimipramine (SURMONTIL®), and combinations thereof.

In specific embodiments, a tricyclic antidepressant used according to the present invention is selected from the group consisting of amitriptyline, butriptyline, clomipramine, desipramine, dosulepin, doxepin, imipramine, lofepramine, nortriptyline, protriptyline, trimipramine, and combinations thereof.

In a particularly preferred embodiment, a tricyclic antidepressant used according tot the present invention is selected from the group consisting of amitriptyline, butriptyline, nortriptyline, protriptyline, and combinations thereof.

Tricyclic antidepressants can be a particularly useful active agent according to the invention in combination with droxidopa and optionally one or more further active agents as described herein. In particular, tricyclic antidepressants are one class of compounds according to the invention that have broad applicability across the various conditions that may be treated using the invention combinations.

Of course, it is well recognized that the tricyclic compounds of the invention can be used in the treatment of depression. Tricyclic antidepressants have also been shown useful in the treatment of several sleep disorders. For example, protriptyline, clomipramine, and imipramine can suppress REM sleep, thus making them useful in preventing narcolepsy. Moreover, as provided in a 2007 report from the American Academy of Sleep Medicine (AASM), tricyclic antidepressants are useful for treating other hypersomnias of central origin, including cataplexy, hypnagogic hallucinations, and sleep paralysis (see Morgenthaler et al., *Sleep* (2007), 30(12): 1705-1727).

Furthermore, tricyclic antidepressants can by useful in the treatment of AD/HD conditions, which are thought to be at least partially caused by dopamine and norepinephrine shortages in the brain's prefrontal cortex. Tricyclic antidepressants block the reuptake of these neurotransmitters and are commonly used in patients for whom psychostimulants are ineffective or contraindicated. TCAs are particularly useful to help limit hyperactivity and impulsivity in AD/HD patients.

In further embodiments of the invention, an active agent used in combination with droxidopa comprises one or more serotonin norepinephrine reuptake inhibiting compounds (SNRIs). As the name implies, SNRIs affect levels of both serotonin and norepinephrine in the CNS. Any compound typically recognized as an SNRI can be used according to the present invention. Non-limiting examples of SNRIs useful according to the invention comprise venlafaxine (EFFEXOR®), desvenlafaxine (PRISTIQ®), milnacipran (DALCIPRAN®), and duloxetine (CYMBALTA®).

According to additional embodiments, an active agent used in combination with droxidopa comprises one or more norepinephrine dopamine reuptake inhibiting compounds (NDRIs). One example of such compounds is bupropion (WELLBUTRIN®). As previously noted, this compound may also be classified as simply an NRI. Both bupropion and its metabolite, radafaxine, may exhibit inhibition of both norepinephrine and dopamine.

In still further embodiments, an active agent used in combination with droxidopa comprises one or more noradrenergic and specific serotonergic antidepressant (NaSSA) compounds. Specific, non-limiting examples of such compounds include mirtazapine (REMERON®) and maprotoline (LUDIOMIL®).

Another group of compounds having antidepressant properties that may be combined with droxidopa according to the invention is benzoxazocine compounds, such as nefopam (including (+)-nefopam). For example, U.S. Patent Application Publication No. 2006/0019940, which is incorporated herein by reference in its entirety, discloses benzoxazocine compounds that may exhibit reuptake inhibition for serotonin, norepinephrine, and dopamine, and such compounds are useful according to the present invention.

In addition to the above compounds, even further types of compounds may be combined with droxidopa according to the invention. Non-limiting examples of further active agents that can be combined with droxidopa include: mood stabilizers (such as lithium, olanzipine, verapamil, quetiapine, lamotrigine, carbamazepine, valproate, oxcarbazepine, risperidone, aripiprazole, and ziprasidone); antipsychotics (such as haloperidol and other butyrophenones, chlorpromazine, fluphenazine, perphenazine, prochlorperazine, and other phenothiazines, and clozapine); serotonin receptor antagonists (5-HT2 and 5-HT3 antagonists) (such as trazodone, ondansetron, tropisetron, katenserin, methysergide, cyproheptadine, and pizotifen); serotonin receptor agonists (5-HT1A receptor agonists) (such as buspirone or BUSPAR®); stimulants [such as caffeine, ADDERALL®, methylphenidate (METADATE®, RITALIN®, or CONCERTA®), pemoline (CYLERT®), dextroamphetamine (DEXEDRINE®, DEXTROSTAT®, or FOCALIN®), methamphetamines (DESOXYN®), mazindol (SANOREX®), or modafinil (PROVIGIL®)]; and gamma-hydroxybutyrate (GHB) (XYREM®).

Although the above compounds are described in terms of classes of compounds and specific compounds, it is understood that there is substantial overlap between certain classes of compounds (such as between mood stabilizers, antipsychotics, antidepressants, and serotonin receptor antagonists). Thus, specific compounds exemplifying a specific class of compounds may also properly be identified with one or more further classes of compounds. Accordingly, the above classifications should not be viewed as limiting the scope of the types of compounds useful in combination with droxidopa for treating the conditions described herein.

Although several specific examples of active agents for use in combination with droxidopa have been disclosed above, such compounds should not be viewed as limiting the invention. Rather, any drug generally recognized as being an antidepressant, antinarcoleptic, anti-insomniac, or AD/HD treatment can be used in combination with droxidopa according to the invention. Moreover, it is possible according to the invention to combine two or more additional active agents with droxidopa for the treatment of the noted conditions.

In specific embodiments, the active agents described above may be combined such that droxidopa is combined with at least one further active agent for use in the treatment of mood disorders, sleep disorders, or attention deficit disorders. In some embodiments, droxidopa may be combined with only one further active agent. In other embodiments, droxidopa may be combined with two or more further active agents. Moreover, when two or more further active agents are combined with droxidopa, the further active agents may be selected from the same or different groups of compounds (e.g., two tricyclic antidepressants or a tricyclic antidepressant and a DDC inhibitor). Non-limiting examples of specific combinations encompasses encompassed by the invention include the following:

a) droxidopa+a DDC inhibiting compound;
b) droxidopa+a COMT inhibiting compound;
c) droxidopa+a cholinesterase inhibiting compound;
d) droxidopa+an antidepressant selected from the group of MAOs, NRIs, SSRIs, tricyclics, SNRIs, NDRIs, and NASSAs;
e) droxidopa+a DDC inhibiting compound+an antidepressant selected from the group of MAOs, NRIs, SSRIs, tricyclics, SNRIs, NDRIs, and NASSAs;
f) droxidopa+a COMT inhibiting compound+an antidepressant selected from the group of MAOs, NRIs, SSRIs, tricyclics, SNRIs, NDRIs, and NASSAs;
g) droxidopa+a cholinesterase inhibiting compound+an antidepressant selected from the group of MAOs, NRIs, SSRIs, tricyclics, SNRIs, NDRIs, and NASSAs;
h) droxidopa+a DDC inhibiting compound+a tricyclic antidepressant;
i) droxidopa+a COMT inhibiting compound+a tricyclic antidepressant;
j) droxidopa+a cholinesterase inhibiting compound+a tricyclic antidepressant;
k) droxidopa+an MAOI+a tricyclic antidepressant;
l) droxidopa+an NRI+a tricyclic antidepressant;
m) droxidopa+an SSRI+a tricyclic antidepressant;
n) droxidopa+one or more of benserazide, carbidopa, difluoromethyldopa, and α-methyldopa+one or more of amitriptyline, butriptyline, nortriptyline, and protriptyline;
o) droxidopa+one or more of entacapone, tolcapone, and nitecapone+one or more of amitriptyline, butriptyline, nortriptyline, and protriptyline;
p) droxidopa+one or more of pyridostigmine, donepezil, rivastigmine, galantamine, tacrine, neostigmine, metrifonate, physostigmine, ambenonium, edrophonium, demarcarium, thiaphysovenine, phenserine, and cymserine+one or more of amitriptyline, butriptyline, nortriptyline, protriptyline;
q) droxidopa+one or more of isocarboxazid, moclobemide, phenelzine, tranylcypromine, selegiline, lazabemide, nialamide, iproniazid, iproclozide, toloxatone, harmala, brofaromine, and benmoxin+one or more of amitriptyline, butriptyline, nortriptyline, protriptyline;
r) droxidopa+one or more of atomoxetine, reboxetine, viloxazine, maprotiline, bupropion, and radafaxine+one or more of amitriptyline, butriptyline, nortriptyline, protriptyline;
s) droxidopa+one or more of fluoxetine, paroxetine, citalopram, escitalopram, fluvoxamine, and sertraline+one or more of amitriptyline, butriptyline, nortriptyline, protriptyline;
t) droxidopa+a DDC inhibiting compound+one or more of a COMT inhibiting compound, a cholinesterase inhibiting compound, and an antidepressant;
u) droxidopa+a DDC inhibiting compound+a COMT inhibiting compound; and
v) droxidopa+one or more of benserazide, carbidopa, difluoromethyldopa, and α-methyldopa+one or more of entacapone, tolcapone, and nitecapone.

III. Methods of Treatment

The present invention, in one embodiment, provides a method for the treatment of mood disorders. Specifically, the invention provides a method for the treatment of depression.

The methods of the invention generally comprise administering droxidopa to a patient suffering from depression. In a specific embodiment, the invention comprises administering droxidopa to a patient exhibiting symptoms of, or having been diagnosed as suffering from, depression.

Depression is typically associated with reduced levels of the neurotransmitters serotonin and norepinephrine, and avenues for increasing neurotransmitter levels within the brain can be effective in treating depression. Interventions for depression thus have included neurotransmitter reuptake inhibitors; however, many reuptake inhibitors also cause undesirable side effects (e.g., weight changes, sleep disruption, and sexual dysfunction).

Droxidopa is converted to norepinephrine by the action of the aromatic L-amino acid decarboxylase known as DDC. Droxidopa is believed to be useful for treating mood disorders, and particularly depression, because of its ability to increase norepinephrine levels via the noted conversion process. Since depression (and other mood disorders) can be linked to reduced norepinephrine levels, treatments that increase the available amount of norepinephrine, particularly in the CNS, are beneficial for treating such conditions.

Mood disorders, such as depression, may be diagnosed when a patient exhibits certain symptoms of such disorders. As previously noted, symptoms of a mood disorder may include: persistent feelings of sadness; feeling hopeless or helpless; having low self-esteem; feeling inadequate; excessive guilt; feelings of wanting to die; loss of interest in usual activities or activities once enjoyed; difficulty with relationships; sleep disturbances; changes in appetite or weight; decreased energy; difficulty concentrating; a decrease in the ability to make decisions; suicidal thoughts or attempts; frequent physical complaints (i.e., headache, stomach ache, fatigue); running away or threats of running away from home; hypersensitivity to failure or rejection; and irritability, hostility, or aggression. Accordingly, treatment of a mood disorder according to the present invention may include eliminating or reducing the frequency or severity of any of the noted symptoms or other symptoms relied upon by a medical professional in making a diagnosis of a mood disorder. Accordingly, in some embodiments, the present invention comprises treating a patient exhibiting at least one symptoms of a mood disorder by administering to the patient droxidopa alone, or in combination with one or more further active agents as described herein, in an amount effective to eliminate or reduce the frequency or severity of the symptom. In particular embodiments, the mood disorder is depression. In other embodiments, the invention may specifically be described as eliminating or reducing the frequency or severity of any one of the specific symptoms of a mood disorder as provided above. In one embodiment, the method comprises eliminating or reducing the frequency or severity of a specific symptom of depression. In such embodiments, the method may comprise administering droxidopa alone or in combination with one or more further active agents as described herein. Effectiveness of the inventive methods may be established through analysis of a treated patient, through self-reporting of the treated patient, or through a diagnosis of effective treatment provided by a medical professional after evaluating the treated patient.

In further embodiments, the invention provides a method for the treatment of sleep disorders. Specifically, the invention provides a method for the treatment of any condition classified as hypersomnia (including narcolepsy, with or without cataplexy, idiopathic hypersomnia, recurrent hypersomnia, and hypersomnia resulting from a medical condition). In another specific embodiment, the invention provides a method for the treatment of insomnia. The methods of the invention generally comprise administering droxidopa to a patient suffering from a condition of hypersomnia or suffering from insomnia.

Although the method of treatment may be described as follows in terms of the specific hypersomnia condition of narcolepsy, it is understood that the inventive method also encompasses treatment of other conditions of hypersomnia, as provided above. As previously pointed out, narcolepsy is typically treated with stimulants and antidepressants (i.e., compositions useful for increasing alertness and reducing fatigue). Accordingly, narcolepsy (and particularly symptoms thereof, such as cataplexy) can be associated with reduced levels of neurotransmitters, such as norepinephrine, and avenues for increasing neurotransmitter levels within the brain can be effective in treating narcolepsy. As droxidopa is converted directly to norepinephrine, it is believed to be useful for treating sleep disorders, and particularly narcolepsy, because of its ability to increase norepinephrine levels via the noted conversion process.

Insomnia may be associated with abnormally elevated norepinephrine levels. Accordingly, the use of one or more drugs that normalize norepinephrine levels may be useful to treat insomnia.

Treatment of a sleep disorder according to the present invention may include a complete cessation of the sleeping disorder or may include reducing the frequency or severity of the sleep disorder. For example, treatment of narcolepsy according to the invention may be evidenced by a complete absence of any narcoleptic events for a specific period of time, a reduction in the frequency of narcoleptic events, or a reduction in the severity of a narcoleptic event. As used herein, a "narcoleptic event" or a "narcoleptic episode" is meant to mean the occurrence of any one or more of the following known symptoms of narcolepsy: excessive daytime sleepiness; cataplexy; sleep paralysis; and hypnagogic hallucinations.

In preferred embodiments, treatment of narcolepsy according to the invention is effective to achieve the complete absence of any narcoleptic events for a time of at least 1 day, at least 2 days, at least 3 days, at least 4 days, at least 5 days, at least 6 days, at least 7 days, at least 2 weeks, at least 3 weeks, at least 4 weeks, at least 5 weeks, at least 6 weeks, at least 2 months, at least 3 months, at least 6 months, or at least 1 year. In specific embodiments, the present invention thus comprises treating a patient suffering from recurrent narcoleptic episodes, wherein the method comprises administering to the patient droxidopa alone, or in combination with one or more further active agents as described herein, in an amount effective to achieve the complete absence of a narcoleptic event for a time as described above. Thus, treatment may be effective to achieve the complete absence of any one or more of the symptoms of narcolepsy previously exhibited by the patient.

In other embodiments, the treatment may be effective to reduce the frequency of narcoleptic events. In particular, the treatment may be effective to reduce the frequency of narcoleptic events to no more than 1 event over the course of a 24-hour day, no more than 1 event over the course of 2 days, no more than 1 event over the course of 3 days, no more than 1 event over the course of 4 days, no more than 1 event over the course of 5 days, no more than one event over the course of 6 days, no more than 1 event over the course of 7 days, no more than 1 event over the course of 2 weeks, no more than one event over the course of 3 weeks, no more than 1 event over the course of 4 weeks, no more than 1 event over the course of 5 weeks, no more than 1 event over the course of 6 weeks, no more than 1 event over the course of 2 months, no more than 1 event over the course of 3 months, no more than one event over the course of 6 months, or no more than 1 event over the course of 1 year. In specific embodiments, the present invention thus comprises treating a patient suffering from recurrent narcoleptic episodes, wherein the method comprises administering to the patient droxidopa alone, or in combination with one or more further active agents as described herein, in an amount effective to reduce the frequency of a narcoleptic event for a time as described above. Thus, the treatment may be effective to reduce the frequency of occurrence of any one or more of the symptoms of narcolepsy previously exhibited by the patient.

In yet further embodiments, treatment may be effective to reduce the severity of a narcoleptic event. For example, the treatment may be effective such that, if the patient does suffer a narcoleptic event, the symptoms of the event do not include complete unconsciousness, do not include complete paralysis, do not include any paralysis, or do not include any hallucinations. In specific embodiments, the present invention thus comprises treating a patient suffering from recurrent narcoleptic episodes, wherein the method comprises administering to the patient droxidopa alone, or in combination with one or more further active agents as described herein, in an amount effective to reduce the severity of the narcoleptic event as described above. Thus, the treatment may be effective to reduce the severity of any one or more of the symptoms of narcolepsy previously exhibited by the patient.

Treatment of insomnia according to the invention may similarly be evidenced by a complete absence of any symptoms of insomnia for a specific period of time, a reduction in the frequency of episodes of insomnia, or a reduction in the severity of an episode of insomnia. As previously pointed out, insomnia may be evidenced by various symptoms. In some patients, insomnia presents as the inability to fall asleep for up to several hours after retiring to sleep at a usual time for the patient. For example, in a patient that normally retires to sleep at 10 p.m., an episode of insomnia may present as the inability to fall asleep until 30 minutes, 1 hour, 2 hours, 3 hours, or even longer after initially retiring to sleep. Episodes of insomnia may typically be present for 2 or more consecutive days, 3 or more consecutive days, 4 or more consecutive days, 5 or more consecutive days, 6 or more consecutive days, 7 or more consecutive days, or even longer. In other cases, insomnia may present as being able to initially fall asleep, but the sleep may be interrupted by one or more awakenings during the sleep period, often accompanied by the inability to fall back asleep for 30 minutes, 1 hour, 2 hours, 3 hours, or even longer.

In preferred embodiments, treatment of insomnia according to the invention is effective to achieve the complete absence of any episode of insomnia. Specifically, episodes of insomnia may be prevented for at least 1 week, at least 2 weeks, at least 3 weeks, at least 4 weeks, at least 5 weeks, at least 6 weeks, at least 2 months, at least 3 months, at least 6 months, or at least 1 year. The present invention thus comprises treating a patient suffering from recurrent episodes of insomnia, wherein the method comprises administering to the patient droxidopa alone, or in combination with one or more further active agents as described herein, in an amount effective to achieve the complete absence of an episode of insomnia for a time as described above. Thus, treatment may be effective to achieve the complete absence of difficulty falling asleep or recurrent awakenings during sleep as previously exhibited by the patient.

In other embodiments, the treatment may be effective to reduce the frequency of episodes of insomnia. In particular, the treatment may be effective to reduce the frequency of episodes of insomnia to no more than 1 episode over the course of 1 week, no more than 1 episode over the course of 2 weeks, no more than 1 episode over the course of 3 weeks, no more than 1 episode over the course of 4 weeks, no more than 1 episode over the course of 5 weeks, no more than 1 episode over the course of 6 weeks, no more than 1 episode over the course of 2 months, no more than 1 episode over the course of 3 months, no more than one episode over the course of 6 months, or no more than 1 episode over the course of 1 year. In specific embodiments, the present invention thus comprises treating a patient suffering from recurrent episodes of insomnia, wherein the method comprises administering to the patient droxidopa alone, or in combination with one or more further active agents as described herein, in an amount effective to reduce the frequency of an episode of insomnia for a time as described above. Thus, the treatment may be effective to reduce the frequency of occurrence of difficulty falling asleep or recurrent awakenings during sleep as previously exhibited by the patient.

In yet further embodiments, treatment may be effective to reduce the severity of an episode of insomnia. For example, the treatment may be effective such that, if the patient does suffer an episode of insomnia, the symptoms of the episode are less severe than previously suffered. For example, difficulty in falling asleep may be reduced in severity such that the patient is able to achieve sleep in less than 1 hour, less than 45 minutes, less than 30 minutes, less than 20 minutes, or less than 15 minutes. Likewise, frequent awakenings may be reduced in severity so that a patient awakens less than 5 times, less than 4 times, less than 3 times, or less than 2 times during an 8 hour period of sleep. Moreover, is a patient suffering from frequent awakenings during sleep does continue to awaken, the severity of the condition is reduced such that the patient is able to re-attain sleep in a time of less than 1 hour, less than 45 minutes, less than 30 minutes, less than 20 minutes, or less than 15 minutes. In specific embodiments, the present invention thus comprises treating a patient suffering from recurrent episodes of insomnia, wherein the method comprises administering to the patient droxidopa alone, or in combination with one or more further active agents as described herein, in an amount effective to reduce the severity of the episodes of insomnia as described above. Thus, the treatment may be effective to reduce the severity of any one or more of the symptoms of insomnia previously exhibited by the patient.

In still another embodiment, the invention provides a method for the treatment of attention deficit disorders (AD/HD). The methods of the invention thus comprise administering droxidopa to a patient suffering from AD/HD.

Historically, stimulants (which affect CNS dopamine levels) have been the drug of choice for treatment of AD/HD; however, recent research indicates other classes of pharmaceuticals can also be effective. For example, the U.S. Food and Drug Administration (FDA) recently approved the use of the NRI STRATTERA® (atomoxetine) for the treatment of AD/HD, which indicates compounds capable of increasing levels of available norepinephrine in the CNS may be effective for treating AD/HD. Again, as droxidopa is converted directly to norepinephrine, it is believed to be useful for treating AD/HD because of its ability to increase norepinephrine levels via the noted conversion process.

As with mood disorders, AD/HD may be diagnosed when a patient exhibits certain symptoms of the disorder. Accordingly, treatment of AD/HD according to the present invention may include eliminating or reducing the frequency or severity of any of the noted symptoms or other symptoms relied upon by a medical professional in making a diagnosis of AD/HD.

Accordingly, in some embodiments, the present invention comprises treating a patient exhibiting at least one symptoms of AD/HD by administering to the patient droxidopa alone, or in combination with one or more further active agents as described herein, in an amount effective to eliminate or reduce the frequency or severity of the symptom. In other embodiments, the invention may specifically be described as eliminating or reducing the frequency or severity of any one of the specific symptoms of AD/HD as described herein. In such embodiments, the method may comprise administering droxidopa alone or in combination with one or more further active agents as described herein. Effectiveness of the inventive methods may be established through analysis of a treated patient, through self-reporting of the treated patient, or through a diagnosis of effective treatment provided by a medical professional after evaluating the treated patient.

It is surprising that a single drug, such as droxidopa, could find use in treating a variety of conditions, such as mood disorders, sleep disorders, and attention deficit disorders. As pointed out previously, droxidopa is useful for increasing norepinephrine levels, particularly in the CNS. Such an increase in norepinephrine levels, in addition to the direct effect of the neurotransmitter, can also have indirect effects that may be beneficial according to the present invention. While not wishing to be bound by theory, increased blood pressure resulting from increased norepinephrine levels (particularly in the CNS through conversion of droxidopa) can lead to increased blood flow in the brain. This can have a significant effect on a variety of conditions. For example, depression, narcolepsy, and AD/HD have all been linked to reduced cerebral blood flow (rCBF). Although focusing on narcolepsy, a recent study by Joo et al., *Neuroimage* (2005), 28(2): p. 410-416 (incorporated herein by reference) disclosed that abnormal cerebral perfusion may explain the characteristic features of narcolepsy, including cataplexy, emotional lability (i.e., depression), and attention deficit. Other clinical studies with compounds, such as methylphenidate, that increase regional cerebral blood flow (perfusion) were found to improve AD/HD. See Lee, et al., *Hum. Brain Mapp.*, (2005), 24(3): 157-164, and Kim, et al., *Yonsei Med J.*, (2001), 42(1): 19-29, both of which are incorporated herein by reference. Surprisingly, the present invention has found that a single drug, such as droxidopa, can form a link to provide successful treatment of a variety of conditions wherein reduced cerebral blood flow may be an underlying factor.

The present invention may thus particularly encompass methods of treating patients suffering from conditions that at least partially arise from reduced blood flow in one or more portions of the brain, such as the cerebrum. The method can particularly comprise administering to the patient droxidopa alone, or in combination with one or more additional active agents, as described herein. Preferably, the administered agent (e.g., droxidopa) or agents (e.g., droxidopa+at least one additional agent) is a therapeutically effective amount that will function to increase brain blood flow (e.g., cerebral blood flow) and thus treat the condition.

The various combinations of one or more further active ingredients with droxidopa, in certain embodiments, are also beneficial for treating the conditions described herein. In certain embodiments, the one or more further active agents provide a conserving effect on the droxidopa. In further embodiments, the one or more further active agents provide a complimentary effect to the action of the droxidopa, preferably eliminating or reducing the frequency or severity of one or more of the symptoms associated with the conditions described herein.

In particular embodiments, droxidopa is combined with one or more DDC inhibitors. Such a combination is particularly beneficial for focusing the effect of the droxidopa in increasing norepinephrine levels. Many DDC inhibitors, such as benserazide and carbidopa, do not enter the central nervous system. Rather, they remain within the periphery where they prevent decarboxylation of compounds (such as levodopa or droxidopa) into the active metabolites (such as norepinephrine). Thus, when a non-CNS DDC inhibitor is administered in combination with droxidopa, the DDC inhibitor prevents decarboxylation of the droxidopa in the periphery and therefore allows more droxidopa to enter the CNS intact. Once within the CNS (and thus segregated from the DDC inhibitor), the droxidopa can be converted to norepinephrine. Accordingly, the combination of a DDC inhibitor with droxidopa can increase the effective ability of the droxidopa to provide norepinephrine within the CNS and the reduce the necessary doses of droxidopa to be effective in treating the conditions described herein.

As previously noted, catechol-O-methyltransferase is directly involved in the metabolism of catecholamines, including dopamine, epinephrine, norepinephrine, and droxidopa. Accordingly, by providing droxidopa in combination with a COMT inhibitor, the effect of the droxidopa to affect the conditions described herein is conserved. Specifically, by inhibiting the action of COMT, the COMT inhibiting compound slows or delays the metabolism of droxidopa (as well as norepinephrine itself). This influences the overall plasma concentration of the droxidopa by increasing both the peak plasma concentration ($C_{max}$) and the half-life of the administered droxidopa. This is particularly beneficial in that it allows for reduced dosages of droxidopa without limiting effective treatment of the conditions described herein. Further, the combination of the COMT inhibitor with droxidopa may be effective for increasing the duration of the droxidopa activity (i.e., increasing the duration of norepinephrine activity), which may allow for a reduction in dosing frequency of the droxidopa. See, for example, U.S. Patent Application Publication 2008/0015181, which is incorporated herein by reference in its entirety.

The combination of droxidopa with an MAOI has a similar effect of conserving bodily norepinephrine levels. In particular embodiments, the MAOI inhibits the action of monoamine oxidase in breaking down norepinephrine, including that formed from the conversion of droxidopa. Accordingly, droxidopa plasma concentrations are positively influenced as the half-life of the droxidopa is increase. This is again particularly beneficial in allowing for reduced droxidopa dosages without limiting effective treatment of the conditions described herein. Moreover, the combination of the MAOI with droxidopa is also effective for increasing droxidopa activity duration, which again may allow for a reduction in dosing frequency of the droxidopa.

In certain embodiments, the combination of droxidopa with cholinesterase inhibitors can be particularly effective. For example, in a specific embodiment, pyridostigmine could be combined with droxidopa, the pyridostigmine enhancing ganglionic neurotransmission while the droxidopa acts to load the postganglionic neuron with norepinephrine.

In still further embodiments, it is particularly useful to combine droxidopa with one or more compounds known to directly increase the availability of norepinephrine in the CNS. As noted above, droxidopa has the effect of being directly converted into norepinephrine; however, the production of norepinephrine can be ineffective if it is undergoing excessive presynaptic reuptake. The combination of droxidopa with a NRI functions to conserve CNS norepinephrine levels.

The combination of droxidopa with the further active ingredients is also particularly useful in the treatment of the conditions described herein. For example, combining droxidopa with one or more antidepressants can provide an additive effect. Moreover, treatments that affect neurotransmitter levels are known to require a "build-up" phase of one to three weeks to reach maximum effectiveness. Thus, it can be useful to combine droxidopa with one or more further active agents that can provide immediate relief to symptoms associated with the conditions described herein. This ability of a combination of droxidopa with an antidepressant and one or more further active agents described herein to be particularly effective in treating depression is illustrated in the Example provided below.

In light of the clear synergistic effect resulting from the combination of a tricyclic antidepressant and droxidopa, the present invention also includes a method of enhancing the therapeutic effectiveness of a tricycle antidepressant in treating any condition for which such compounds are used. For example, the combination of droxidopa and tricyclic antidepressants could be used to enhance the therapeutic effectiveness of such antidepressants to treat mood disorders, sleep disorders, and attention deficit disorders as noted herein, but also to enhance treatment of neuropathic pain, nocturnal enuresis, headaches (including migraines), anxiety, bulimia nervosa, irritable bowel syndrome, persistent hiccups, and interstitial cystitis.

IV. Biologically Active Variants

Biologically active variants of the various compounds disclosed herein as active agents are particularly also encompassed by the invention. Such variants should retain the general biological activity of the original compounds; however, the presence of additional activities would not necessarily limit the use thereof in the present invention. Such activity may be evaluated using standard testing methods and bioassays recognizable by the skilled artisan in the field as generally being useful for identifying such activity.

According to one embodiment of the invention, suitable biologically active variants comprise analogues and derivatives of the compounds described herein. Indeed, a single compound, such as those described herein, may give rise to an entire family of analogues or derivatives having similar activity and, therefore, usefulness according to the present invention. Likewise, a single compound, such as those described herein, may represent a single family member of a greater class of compounds useful according to the present invention. Accordingly, the present invention fully encompasses not only the compounds described herein, but analogues and derivatives of such compounds, particularly those identifiable by methods commonly known in the art and recognizable to the skilled artisan.

The compounds disclosed herein as active agents may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are will known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular to the extent of 95% or more, or 98% or more, including 100%.

The compounds described herein as active agents can also be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry: Reactions, Mechanisms and Structure, $4^{th}$ Ed. (New York: Wiley-Interscience, 1992), which is incorporated herein by reference.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the active agent compounds described herein. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. In preferred embodiments, the compounds of this invention possess anti-proliferative activity against abnormally proliferating cells, or are metabolized to a compound that exhibits such activity.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed active agents to achieve a desired effect.

V. Pharmaceutical Compositions

While it is possible for individual active agent compounds used in the methods of the present invention to be administered in the raw chemical form, it is preferred for the compounds to be delivered as a pharmaceutical composition. Accordingly, there are provided by the present invention pharmaceutical compositions comprising one or more compounds described herein as active agents. As such, the compositions used in the methods of the present invention comprise the pharmaceutically active compounds, as described above, or pharmaceutically acceptable esters, amides, salts, solvates, analogs, derivatives, or prodrugs thereof. Further, the compositions can be prepared and delivered in a variety of combinations. For example, the composition can comprise a single composition containing all of the active ingredients. Alternately, the composition can comprise multiple compositions comprising separate active ingredients but intended to be administered simultaneously, in succession, or in otherwise close proximity of time.

The active agent compounds described herein can be prepared and delivered together with one or more pharmaceutically acceptable carriers therefore, and optionally, other therapeutic ingredients. Carriers should be acceptable in that they are compatible with any other ingredients of the composition and not harmful to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Compositions may include short-term, rapid-onset, rapid-offset, controlled release, sustained release, delayed release, and pulsatile release compositions, providing the compositions achieve administration of a compound as described herein. See *Remington's Pharmaceutical Sciences* (18$^{th}$ ed.; Mack Publishing Company, Eaton, Pa., 1990), herein incorporated by reference in its entirety.

Pharmaceutical compositions for use in the methods of the invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

The pharmaceutical compositions may be conveniently made available in a unit dosage form, whereby such compositions may be prepared by any of the methods generally known in the pharmaceutical arts. Generally speaking, such methods of preparation comprise combining (by various methods) the active compounds of the invention with a suitable carrier or other adjuvant, which may consist of one or more ingredients. The combination of the active ingredients with the one or more adjuvants is then physically treated to present the composition in a suitable form for delivery (e.g., shaping into a tablet or forming an aqueous suspension).

Pharmaceutical compositions suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions according to the present invention.

In one embodiment, an active agent compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the active agent compounds may be made using a physiologically degradable composition, such as gelatin. Such hard capsules comprise the compound, and may further comprise additional ingredients including, for example, an inert solid diluent such as calcium carbonate, calcium phosphate, or kaolin. Soft gelatin capsules containing the compound may be made using a physiologically degradable composition, such as gelatin. Such soft capsules comprise the compound, which may be mixed with water or an oil medium such as peanut oil, liquid paraffin, or olive oil.

Sublingual tablets are designed to dissolve very rapidly. Examples of such compositions include ergotamine tartrate, isosorbide dinitrate, and isoproterenol HCL. The compositions of these tablets contain, in addition to the drug, various soluble excipients, such as lactose, powdered sucrose, dextrose, and mannitol. The solid dosage forms of the present invention may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins (such as those commercially available under the trade name EUDRAGIT®), zein, shellac, and polysaccharides.

Powdered and granular compositions of a pharmaceutical preparation may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions.

Liquid compositions of pharmaceutical compositions which are suitable for oral administration may be prepared, packaged, and sold either in liquid form or in the form of a dry product intended for reconstitution with water or another suitable vehicle prior to use.

A tablet containing one or more active agent compounds described herein may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents.

Adjuvants or accessory ingredients for use in the compositions can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the composition according to the present invention may be anionic, cationic, amphoteric, or nonionic surface active agents. Stabilizers may be included in the compositions to inhibit or lessen reactions leading to decomposition of the active agents, such as oxidative reactions.

Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agents over a prolonged period of time), and may or may not also be delayed release. Sustained release compositions are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compositions for use in the methods of the invention may also be administered transdermally, wherein the active agents are incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agents are contained in a layer separate from the adhesive layer. Both types of patches also generally contain a backing layer and a liner that is removed prior to attachment to the recipient's skin. Transdermal drug delivery patches may also be comprised of a reservoir underlying the backing layer that is separated from the skin of the recipient by a semi-permeable membrane and adhesive layer. Transdermal drug delivery may occur through passive diffusion, electrotransport, or iontophoresis.

Compositions for rectal delivery include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

Topical compositions may be in any form suitable and readily known in the art for delivery of active agents to the body surface, including dermally, buccally, and sublingually. Typical examples of topical compositions include ointments, creams, gels, pastes, and solutions. Compositions for administration in the mouth include lozenges.

In certain embodiments, the compounds and compositions disclosed herein can be delivered via a medical device. Such delivery can generally be via any insertable or implantable medical device, including, but not limited to stents, catheters, balloon catheters, shunts, or coils. In one embodiment, the present invention provides medical devices, such as stents, the surface of which is coated with a compound or composition as described herein. The medical device of this invention can be used, for example, in any application for treating, preventing, or otherwise affecting the course of a disease or condition, such as those disclosed herein.

In another embodiment of the invention, pharmaceutical compositions comprising one or more active agents described herein are administered intermittently. Administration of the therapeutically effective dose may be achieved in a continuous manner, as for example with a sustained-release composition, or it may be achieved according to a desired daily dosage regimen, as for example with one, two, three, or more administrations per day. By "time period of discontinuance" is intended a discontinuing of the continuous sustained-released or daily administration of the composition. The time period of discontinuance may be longer or shorter than the period of continuous sustained-release or daily administration. During the time period of discontinuance, the level of the components of the composition in the relevant tissue is substantially below the maximum level obtained during the treatment. The preferred length of the discontinuance period depends on the concentration of the effective dose and the form of composition used. The discontinuance period can be at least 2 days, at least 4 days or at least 1 week. In other embodiments, the period of discontinuance is at least 1 month, 2 months, 3 months, 4 months or greater. When a sustained-release composition is used, the discontinuance period must be extended to account for the greater residence time of the composition in the body. Alternatively, the frequency of administration of the effective dose of the sustained-release composition can be decreased accordingly. An intermittent schedule of administration of an inventive composition can continue until the desired therapeutic effect, and ultimately treatment of the disease or disorder, is achieved.

Administration of the composition comprises administering a pharmaceutically active agent as described herein or administering one or more pharmaceutically active agents described herein in combination with one or more further pharmaceutically active agents (i.e., co-administration). Accordingly, it is recognized that the pharmaceutically active agents described herein can be administered in a fixed combination (i.e., a single pharmaceutical composition that contains both active agents). Alternatively, the pharmaceutically active agents may be administered simultaneously (i.e., separate compositions administered at the same time). In another embodiment, the pharmaceutically active agents are administered sequentially (i.e., administration of one or more pharmaceutically active agents followed by separate administration or one or more pharmaceutically active agents). One of skill in the art will recognized that the most preferred method of administration will allow the desired therapeutic effect.

Delivery of a therapeutically effective amount of a composition according to the invention may be obtained via administration of a therapeutically effective dose of the composition. Accordingly, in one embodiment, a therapeutically effective amount is an amount effective to treat depression. In another embodiment, a therapeutically effective amount is an amount effective to treat a narcolepsy. In yet another embodiment, a therapeutically effective amount is an amount effective to treat AD/HD. In further embodiments, a therapeutically effective amount is an amount effective to treat a symptom of depression. In still another embodiment, a therapeutically effective amount is an amount effective to treat a symptom of narcolepsy. In yet another embodiment, a therapeutically effective amount is an amount effective to treat a symptom of AD/HD.

The active agents included in the pharmaceutical composition are present in an amount sufficient to deliver to a patient a therapeutic amount of an active ingredient in vivo in the absence of serious toxic effects. The concentration of active agent in the drug composition will depend on absorption, inactivation, and excretion rates of the drug as well as other factors known to those of skill in the art. It is to be noted that dosage values will also vary with the severity of the condition being treated. It is further understood that for any particular subject, specific dosage regimens should be adjusted according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time A therapeutically effective amount according to the invention can be determined based on the bodyweight of the recipient. Alternatively, a therapeutically effective amount can be described in terms of a fixed dose. In still further embodiments, a therapeutically effective amount of one or more active agents disclosed herein can be described in terms of the peak plasma concentration achieved by administration of the active agents. Of course, it is understood that the therapeutic amount could be divided into a number of fractional dosages administered throughout the day. The effective dosage range of pharmaceutically acceptable salts and prodrugs can be calculated based on the weight of the parent nucleoside to be delivered. If a salt or prodrug exhibits activity in itself, the effective dosage can be estimated as above using the weight of the salt or prodrug, or by other means known to those skilled in the art.

It is contemplated that compositions of the invention comprising one or more active agents described herein will be administered in therapeutically effective amounts to a mammal, preferably a human. An effective dose of a compound or composition for treatment of any of the conditions or diseases described herein can be readily determined by the use of conventional techniques and by observing results obtained under analogous circumstances. The effective amount of the compositions would be expected to vary according to the weight, sex, age, and medical history of the subject. Of course, other factors could also influence the effective amount of the composition to be delivered, including, but not limited to, the specific disease involved, the degree of involvement or the severity of the disease, the response of the individual patient, the particular compound administered, the mode of administration, the bioavailability characteristics of the preparation administered, the dose regimen selected, and the use of concomitant medication. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) *Harrison's Principles of Internal Medicine* 13 ed., 1814-1882, herein incorporated by reference.

In certain embodiments, the therapeutically effective amount of droxidopa can encompass varying ranges, and the appropriate range could be determined based upon the severity of the condition being treated and the presence of one or more additional compounds with which the droxidopa is combined. In specific embodiments, a therapeutically effective amount of droxidopa comprises about 10 mg to about 2 g, about 10 mg to about 1 g, about 20 mg to about 900 mg, about 30 mg to about 850 mg, about 40 mg to about 800 mg, about 50 mg to about 750 mg, about 60 mg to about 700 mg, about 70 mg to about 650 mg, about 80 mg to about 600 mg, about 90 mg to about 550 mg, about 100 mg to about 500 mg, about 100 mg to about 400 mg, or about 100 mg to about 300 mg.

A therapeutically effective amount of the one or more additional compounds that can be combined with droxidopa according to the invention can be determined in relation to the amount of droxidopa included in the dosage form and the desired ratio of droxidopa to the additional compound(s).

Advantageously, the present invention allows for great flexibility in formulating combinations. For example, the conserving effects provided by the one or more additional compounds can allow for using droxidopa in a lesser amount and still achieve the same, or better, therapeutic effects achieved using droxidopa alone. Likewise, it is possible to increase the therapeutic effects of droxidopa by using an amount of the one or more additional compounds that is less than the typically recommended dosage for the one or more additional compounds. The one or more additional compounds combined with droxidopa according to the invention can be included in amount typically recommended for use of the compounds alone.

In one embodiment, the ratio of droxidopa to the one or more additional compounds is in the range of about 500:1 to about 1:10. In further embodiments, the ratio of droxidopa to the additional compound(s) is in the range of about 250:1 to about 1:5, about 100:1 to about 1:2, about 80:1 to about 1:1, about 50:1 to about 2:1, or about 20:1 to about 3:1.

VI. Articles of Manufacture

The present invention also includes an article of manufacture providing a composition comprising one or more active agents described herein. The article of manufacture can include a vial or other container that contains a composition suitable for use according to the present invention together with any carrier, either dried or in liquid form. In particular, the article of manufacture can comprise a kit including a container with a composition according to the invention. In such a kit, the composition can be delivered in a variety of combinations. For example, the composition can comprise a single dosage comprising all of the active ingredients. Alternately, where more than one active ingredient is provided, the composition can comprise multiple dosages, each comprising one or more active ingredients, the dosages being intended for administration in combination, in succession, or in other close proximity of time. For example, the dosages could be solid forms (e.g., tablets, caplets, capsules, or the like) or liquid forms (e.g., vials), each comprising a single active ingredient, but being provided in blister packs, bags, or the like, for administration in combination.

The article of manufacture further includes instructions in the form of a label on the container and/or in the form of an insert included in a box in which the container is packaged, for carrying out the inventive method. The instructions can also be printed on the box in which the vial is packaged. The instructions contain information such as sufficient dosage and administration information to allow the subject or a worker in the field to administer the pharmaceutical composition. A worker in the field encompasses any doctor, nurse, technician, spouse, or other caregiver that might administer the composition. The pharmaceutical composition can also be self-administered by the subject.

The present invention will now be described with specific reference to various examples. The following examples are not intended to be limiting of the invention and are rather provided as exemplary embodiments.

EXAMPLE

Treatment of Depression

The effect of droxidopa, alone or in combination with other drugs, in the treatment of depression was evaluated using the murine Forced Swim Test (FST), a mouse model of depression commonly used to evaluate antidepressive drugs. Depression (i.e., "learned helplessness" as evaluated by the FST model) was measured using the method of Porsolt et al., *Arch. Int. Pharmacodyn.* (1977), 229: 327-336. Briefly, male CD-1 mice weighing 22 g (±2 g) were fasted overnight prior to testing. The mice were randomized into 11 groups of 10 mice each. Mice in each group were treated with the vehicle alone, a drug, or a drug composition as outlined in Table 1 and returned to their respective groups.

TABLE 1

| Group | Test Composition | Route | Conc. mg/ml | Dosage ml/kg | Dosage mg/kg |
|---|---|---|---|---|---|
| 1 | Vehicle | Intraperitoneal | NA | 10 | NA |
| 2 | Desipramine | Intraperitoneal | 5 | 10 | 10 |
| 3 | Entacapone | Intraperitoneal |  | 10 | 30 |
| 4 | Fluoxetine | Intraperitoneal |  | 10 | 18 |
| 5 | Venlafaxine | Intraperitoneal |  | 10 | 10 |
| 6 | Amitriptyline | Intraperitoneal |  | 10 | 10 |
| 7 | Droxidopa + Carbidopa | Intraperitoneal |  | 10 | 400 20 |
| 8 | Droxidopa + Carbidopa + Entacapone | Intraperitoneal |  | 10 | 400 20 30 |
| 9 | Droxidopa + Carbidopa + Fluoxetine | Intraperitoneal |  | 10 | 400 20 18 |
| 10 | Droxidopa + Carbidopa + Venlafaxine | Intraperitoneal |  | 10 | 400 20 10 |
| 11 | Droxidopa + Carbidopa + Amitriptyline | Intraperitoneal |  | 10 | 400 20 10 |

In Table 1, the vehicle—2% TWEEN® 80 (i.e., polysorbate 80)—was included in all test compositions. One hour after dosing, the test mice were placed in a 1 liter volume glass beaker (height: 14.5 cm, diameter: 10.5 cm) containing water 6 cm in height at room temperature (22 to 24° C.) for 6 minutes. The duration of animal immobility within the last 4 minutes was then recorded. A mouse was judged to be immobile when it ceased struggling and remained floating in the water making only those movements necessary to keep its head above water. Data were analyzed by ANOVA for significant differences in group means, followed by T-test to distinguish statistically significant groups as appropriate.

As illustrated in FIG. 1 and FIG. 2, test mice treated with the vehicle alone displayed a pattern of immobility that was slightly depressed relative to the historical control values (i.e., an average time immobile of 138.3±20.4 sec versus historical control values of 190±30 sec). The lower than normal value for the control group was likely due to 2 outlying animals (as seen in FIG. 2). Treatment with desipramine, entacapone, fluoxetine, or venlafaxine alone also did not significantly decrease the length of time that the mice spent immobile (136.4 sec for desipramine, 129.9 sec for entacapone, 158.2 sec for fluoxetine, and 117.5 sec for venlafaxine). Further, the time spent immobile was not decreased by administration of droxidopa+carbidopa (191.8 sec), droxidopa+carbidopa+entacapone (161.1 sec), or droxidopa+carbidopa+fluoxetine (139.3 sec). Treatment with amitriptyline alone caused a significant decrease in the length of time the test mice spent immobile (60.0 sec). Surprisingly, treatment with droxidopa+carbidopa+amitriptyline resulted in a significant decrease in the length of time animals spent immobile (20.0 sec, $p<0.005$). Moreover, the addition of droxidopa+carbidopa to amitriptyline resulted in a significant decrease in the depression score of mice over that seen with amitriptyline alone ($p<0.05$).

As seen in FIG. 1, treatment with desipramine, fluoxetine, or venlafaxine failed to decrease depression even though these compounds have been reported to be active in this model (see Dableh et al., *Eur. J. Pharmacol.* (2005), 507: 99-105, and Dhir et al., *Pharmacol.* (2007), 80: 239-43). However the validity of the model was confirmed by the finding that 10 mg/kg of amitriptyline induced a significant decrease in the length of time the test mice spent immobile. Further, the degree of reduction in the time spent immobile induced by amitriptyline is similar to that previously reported in the literature (see Lamberti et al., *Br. J. Pharmacol.* (1998), 123: 1331-1336). By contrast, the addition of droxidopa+ carbidopa to amitriptyline resulted in significantly lower immobility times, indicating that droxidopa acted synergistically with amitriptyline. Although not wishing to be bound by theory, it is believed that the synergistic effect seen with this specific combination may arise because from the specific action of tricyclic antidepressants (amitriptyline being one example) on the noradrenergic system and the augmenting effect of droxidopa on the action of tricyclic antidepressants.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating an attention deficit disorder, the method comprising administering a therapeutically effective amount of active agents to a subject in need of treatment of the condition, the active agents comprising droxidopa, or a pharmaceutically acceptable ester, amide, or salt thereof in combination with a DOPA decarboxylase inhibiting compound selected from the group consisting of benserazide, carbidopa, difluoromethyldopa, α-methyldopa, and combinations thereof.

2. The method of claim 1, wherein the DOPA decarboxylase inhibiting compound is carbidopa.

3. The method of claim 1, wherein the active agents are administered in one or more pharmaceutical compositions.

4. The method of claim 3, wherein the active agents are formulated in the same pharmaceutical composition.

5. The method of claim 3, wherein the droxidopa is administered in a controlled release form.

6. The method of claim 3, wherein the droxidopa is administered in a sustained release form.

7. The method of claim 1, wherein the attention deficit disorder is Attention-Deficit/Hyperactivity Disorder (AD/HD).

8. The method of claim 7, wherein the subject is suffering from at least one symptom of AD/HD, and the method comprises eliminating the symptom, reducing the severity of the symptom, or reducing the frequency of occurrence of the symptom.

9. The method of claim 1, wherein the droxidopa is administered in a first pharmaceutical composition and the one or more additional active agents are administered in a pharmaceutical composition separate from the droxidopa.

10. The method of claim 1, wherein droxidopa is administered in the form of a mixture enantiomerically enriched in the L-threo isomer.

* * * * *

UNITED STATES PATENT AND TRADEMARK OFFICE
CERTIFICATE OF CORRECTION

PATENT NO.       : 8,383,681 B2
APPLICATION NO.  : 12/116560
DATED            : February 26, 2013
INVENTOR(S)      : Michael J. Roberts et al.

It is certified that error appears in the above-identified patent and that said Letters Patent is hereby corrected as shown below:

Title Page:

Related U.S. Application Data should read

Item --(60)   Provisional Application 60/916,497, filed May 7, 2007--

Signed and Sealed this
Twenty-seventh Day of August, 2013

Teresa Stanek Rea
*Acting Director of the United States Patent and Trademark Office*